United States Patent
Tilly et al.

(10) Patent No.: US 7,850,984 B2
(45) Date of Patent: *Dec. 14, 2010

(54) PROTECTION OF THE FEMALE REPRODUCTIVE SYSTEM FROM NATURAL AND ARTIFICIAL INSULTS

(75) Inventors: Jonathan L. Tilly, Windham, NH (US); Richard N. Kolesnick, New York, NY (US)

(73) Assignees: The General Hospital Corporation, Boston, MA (US); Memorial Sloan-Kettering Cancer Center, New York, NY (US)

( * ) Notice: Subject to any disclaimer, the term of this patent is extended or adjusted under 35 U.S.C. 154(b) by 2066 days.

This patent is subject to a terminal disclaimer.

(21) Appl. No.: 10/217,259

(22) Filed: Aug. 12, 2002

(65) Prior Publication Data

US 2003/0157086 A1   Aug. 21, 2003

Related U.S. Application Data

(63) Continuation-in-part of application No. 09/503,852, filed on Feb. 15, 2000, now Pat. No. 7,195,775.

(51) Int. Cl.
*A61F 2/02* (2006.01)
(52) U.S. Cl. .................................................. 424/423
(58) Field of Classification Search ................. 424/423, 424/430, 434
See application file for complete search history.

(56) References Cited

U.S. PATENT DOCUMENTS

| | | | |
|---|---|---|---|
| 5,712,262 A | 1/1998 | Spiegel | |
| 5,773,278 A | 6/1998 | Schuchman et al. | |
| 5,877,167 A | 3/1999 | Igarashi et al. | |
| 2007/0157331 A1 | 7/2007 | Tilly et al. | |

OTHER PUBLICATIONS

Moirta et al, oocye Apoptosis is Supressed by Disrutpion of the Acid Sphingomyelinase gene or by Sphingosine—1-phosphate therapy, Nature Medicine, (Oct. 2000) vol. 6, No. 10, pp. 1109-1114.*

Gong et al., "The tyrosine kinase c-Abl regulates p73 in apoptotic response to cisplatin-induced DNA damage", *Nature*, (1999) 399:806-809.

Springer et al., "Involvement of Apoptosis in 4-Vinylcyclohexene Diepoxide-Induced Ovotoxicity in Rats", *Toxicol. Appl. Pharmacol.*, (1996) 139:394-401.

(Continued)

*Primary Examiner*—Carlos A Azpuru
(74) *Attorney, Agent, or Firm*—Edwards Angell Palmer & Dodge LLP; Peter C. Lauro, Esq.; Melissa Hunter-Ensor, Esq.

(57) ABSTRACT

Described are methods for protecting the female reproductive system against natural and artificial insults by administering to women a composition comprising an agent that antagonizes one or more acid sphingomyelinase (ASMase) gene products. Specifically, methods disclosed herein serve to protect women's germline from damage resulting from cancer therapy regimens including chemotherapy or radiotherapy. In one aspect, the method preserves, enhances, or revives ovarian function in women, by administering to women a composition containing sphingosine-1-phosphate, or an analog thereof. Also disclosed are methods to prevent or ameliorate menopausal syndromes and to improve in vitro fertilization techniques.

27 Claims, 8 Drawing Sheets

OTHER PUBLICATIONS

Figure 1:
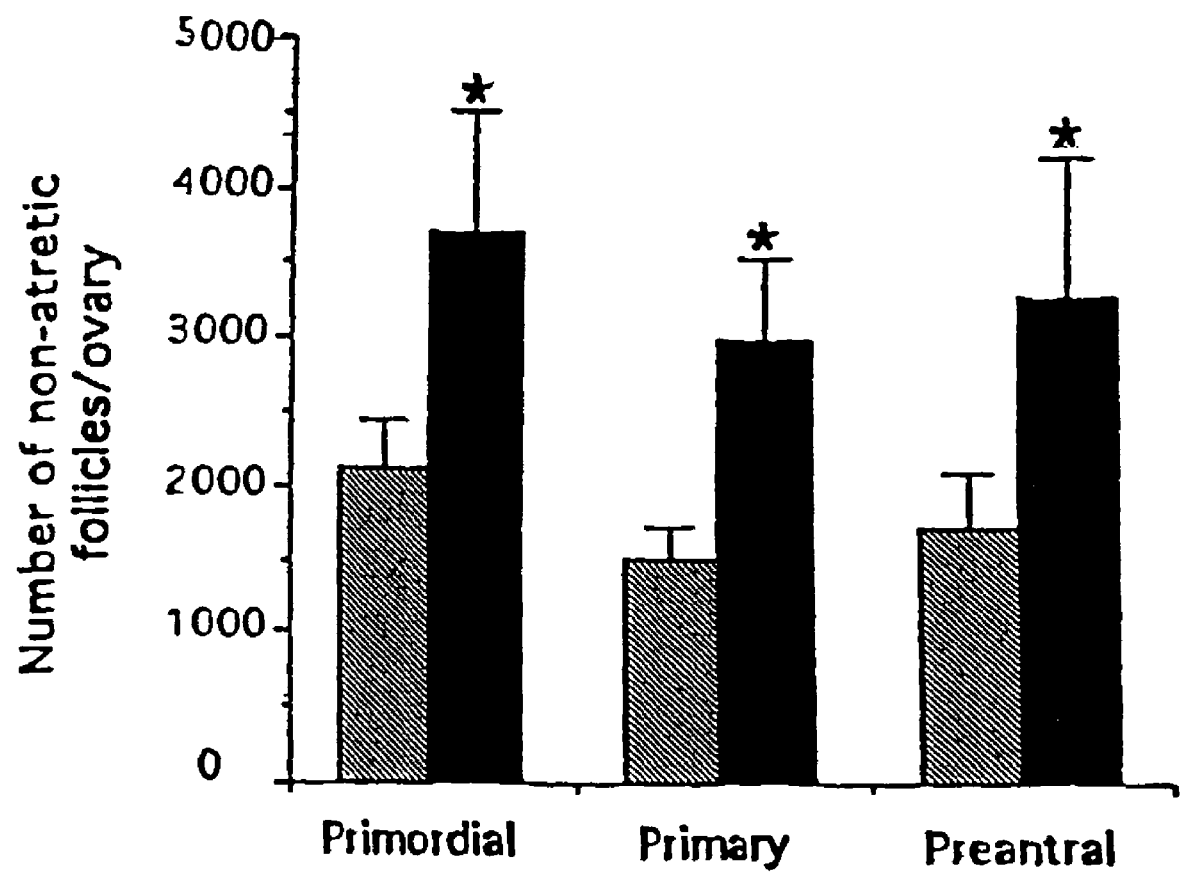

Perez and Tilly, "Cumulus cells are required for the increased apooptotic potential in oocytes of aged mice", *Human Reproduction* (1997) 12:2781-2783.

Perez et al., "Prolongation of ovarian lifespan into advanced chronological age by *Bax*-deficiency", *Nature Genetics*, (1999) 21:200-203.

Kugu et al., "Analysis of apoptosis and expression of *bcl*-2 gene family members in th ehuman and baboon ovary", *Cell Death and Differentiation*, (1998) 5:67-76.

Flaws et al., "Vasoactive intestinal peptide-mediated suppression of apoptosis in the Ovary: Potential Mechanisms of Action and Evidence of a conserved antiatreogenic role through evolution", *Endocrinol.* (1995) 136:4351-4359.

Tilly et al., "Epidermal growth factor and basic fibroblast growth factor suppress the spontaneous onset of apoptosis in cultured rat ovarian granulosa cells and follicles by a tyrosine kinase-dependent mechanism", *Mol. Endocrinol.*, (1992) 6:1942-1950.

Johnson et al., "Susceptibility of Avian Ovarian Granulosa cells to apoptosis is dependent upon stage of follicle development and is related to endogenous lvels of *bcl*-xlong gene expression", *Endocrinol.* (1996) 137:2059-2066.

Greco RM. et al., "Differences in cell division and thymidine incorporation with rat and primate fibroblasts in collagen lattices", *Tissue Cell.*, (1992) 24:6 843-851.

Bergeron, L., et al., "Defects in Regulation of Apoptosis in Caspase-2-Deficient Mice", Genes. Dev., vol. 12, pp. 1304-1314 (1998).

Goetzl, E., et al., "Diversity of Cellular Receptors and Functions for the Lysophospholipid Growth Factors Lysophosphatidic Acid and Sphingosine 1-Phosphate", FASEB J., vol. 12, No. 15, pp. 1589-1598 (1998).

Perez, G., et al., "Apoptosis-Associated Signaling Pathways Are Required for Chemotherapy-Mediated Female Germ Cell Destruction", Nat. Med., vol. 3, No. 11, pp. 1228-1232 (1997).

Cuvillier, O., et al., "Suppression of Ceramide-Mediated Programmed Cell Death by Sphingosine-1-Phosphate", Nature, vol. 381, No. 6585, pp. 800-803 (1996).

K., Horinouchi, et al., "Acid Sphingomyelinase Decicient Mice: A Model of Types A and B Niemann-Pick Disease", Nat. Genet., vol. 10, No. 3, pp. 288-293 (1995).

Edsall, L. C., et al., "Involvement of Sphingosine 1-Phosphate in Nerve Growth Factor-Mediated Neuronal Survival and Differentiation", J. Neurosci., vol. 17, pp. 6952-6960 (1977).

Abstract, Tilly et al., "Sphingolipid signaling in gonadal development and function" abstract No. 623565, Chem. Abstracts vol. 131, No. 349341 (1999).

Abstract, Morita et al., "Oocyte apoptosies is suppressed by disruption of the acid sphingomyelinase gene or by sphingosine-1-phosphate therapy", abstract No. 736446, Chem. Abstracts, vol. 134, No. 25322 (2000).

Abstract, Casper et al., "Protecting the Female Germ Line from Cancer Therapy", Elsevier Science Publishers, Amsterdam. No. 2000375706 (2000).

Morita, Y., et al., "Oocyte Apoptosis: Like Sand Through an Hourglass", Dev. Biol., vol. 213, No. 1, pp. 1-17 (1999).

Morita, Y., et al., "Requirement for Phosphatidylinositol-3"-Kinase in Cytokine-Mediated Germ Cell Survival During Fetal Oogenesis in the Mouse", Endocrinology, vol. 140, No. 2, pp. 941-949 (1999).

Morita, Y., et al., "Targeted Expression of Bcl-2 in Mouse Oocytes Inhibits Ovarian Follicle Atresia and Prevents Spontaneous and Chemotherapy-Induced Oocyte Apoptosis In Vitro", Mol. Endocrinology, vol. 13, No. 6, pp. 841-850 (1999).

Hla, T., et al., "Sphingosine-1-Phosphate: Extracellular Mediator or Intracellular Second Messenger?", Biochem. Pharmacol, vol. 58, No. 2, pp. 201-207 (1999).

Perez, G., et al., "Fragmentation and Death (A.K.A. Apoptosis) of Ovulated Oocytes", Mol. Human Reprod., vol. 5, No. 5, pp. 414-420 (1999).

Reynolds, T.., "Cell Death Genes May Hold Clues to Preserving Fertility After Chemotherapy", J. Nat'l Cancer Inst., vol. 91, No. 8, pp. 664-666 (1999).

Perez, G., et al., "Prolongation of Ovarian Lifespan Into Advanced Chronological Age by Bax-Deficiency", Nature Genet., vol. 21, No. 2, pp. 200-203 (1999).

Spiegel, S., Sphingosine 1-Phosphate: A Prototype of a New Class of Second Messengers, J. Leukocyte Biol., vol. 65, No. 3, pp. 341-344 (1999).

Spiegel, S., et al., "Sphingosine-1-Phosphate in Cell Growth and Cell Death", Ann. N.Y. Acad. Sci., vol. 845, pp. 11-18 (1998).

Gougeon, Endocr Rev. 17, 121 (1996).

Morita, Y. et al., Nat. Med. 6, 1109-1114 (2000).

Waxman, Soc. Med. 76,144 (1983).

Familiari et al., Hum. Reprod. 8, 2080 (1993).

Ried & Jaffee, Semin. Roentgenol. 29, 6 (1994).

Reichman & Green, Monogr. Natl. Cancer Inst. 16, 125 (1994).

Tilly & Ratts, Contemp. Obstet. Gynecol. 41, 59 (1996).

Tilly, Rev. Reprod. 1, 162 (1996).

Tilly et al., Cell Death Differ. 4, 180 (1997).

Tilly et al., Endocrinology 136, 1394 (1995).

Tilly et al., Endocrinology 136-232 (1995).

Adams & Cory, Science 281, 1322 (1998).

Green, Cell 94,695 (1998).

Thornberry & Lazebnik, Science 281, 1312 (1998).

Reed, Oncogene 17, 3225 (1998).

Korsmeyer, Cancer Res. 59,1693 (1999).

Keren-Tal et al., Exp. Cell Res. 218, 283 (1995).

Makrigiannakis et al., J. Clin. Endocrinol. Metab. 85, 449 (2000).

Ratts et al., Endocrinology 136, 3665 (1995).

Knudson et al., Science 270,99 (1995).

Flaws et al., Endocrinology 136, 5042 (1995).

Maravei et al., Cell Death Differ. 4, 707 (1997).

Boone & Tsang, Biol. Reprod. 58, 1533 (1998).

Hannun, Science 274, 1855 (1996).

Kolesnick & Kronke, Annu. Rev. Physiol. 60:643 (1998).

Witty et al., Endocrinology 137, 5269 (1996).

Kaipia et al., Endocrinology 137, 4864 (1996).

Martimbeau & Tilly, Clin. Endocrinol. 46, 241 (1997).

Spiegal et al., Curr. Opin. Cell Biol. 8, 159 (1996).

Hofmann & Dixit, Trends Biochem. Sci 23, 374 (1998).

Watts et al., Cell Death Differ. 6, 105 (1999).

Ko & Prives, Genes Dev. 10, 1054 (1996).

Ding et al., Crit. Rev. Oncog. 9, 83 (1998).

Declaration of Dr. Jonathan L. Tilly Under 37 C.F.R. §1.132 dated Feb. 7, 2008.

Schissel, S. et al, "Secretory Sphingomyellnase, a Product of the Acid Sphingomyelinase Gene, Can Hydrolyze Atherogenic Lipoproteins at Neutral pH", The Journal of Biological chemistry, vol. 273, No. 5, pp. 2738-2746Issue of Jan. 30, 1998.

Levran O. et al., "Niemann-Pick disease: A Frequent Missense Mutation in the Acid Sphingomyelinase Gene of Ashkenazl Jewish Type A and B Patients", Proc. Natl. Acad. Sci. USA vol. 88, pp. 3748-3752, May 1991.

\* cited by examiner

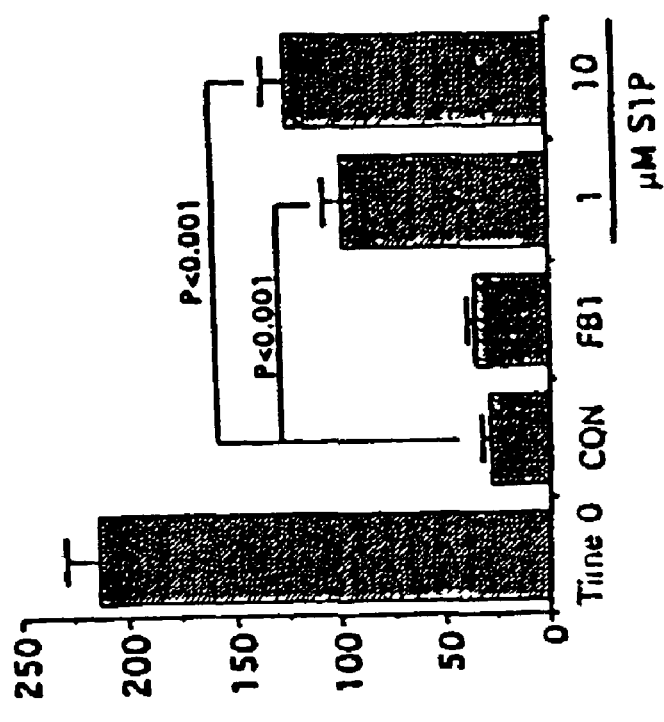
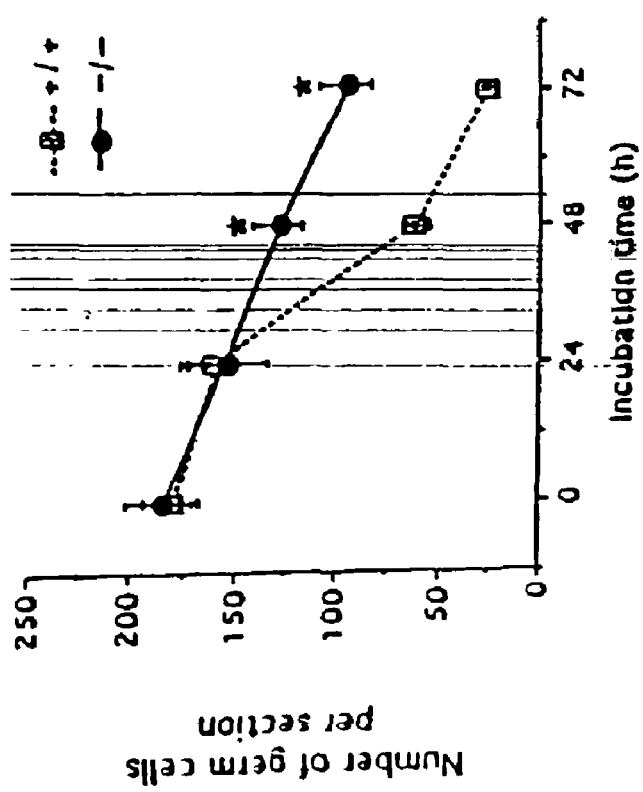
Figure 2b
Figure 2a

Figure 3D:
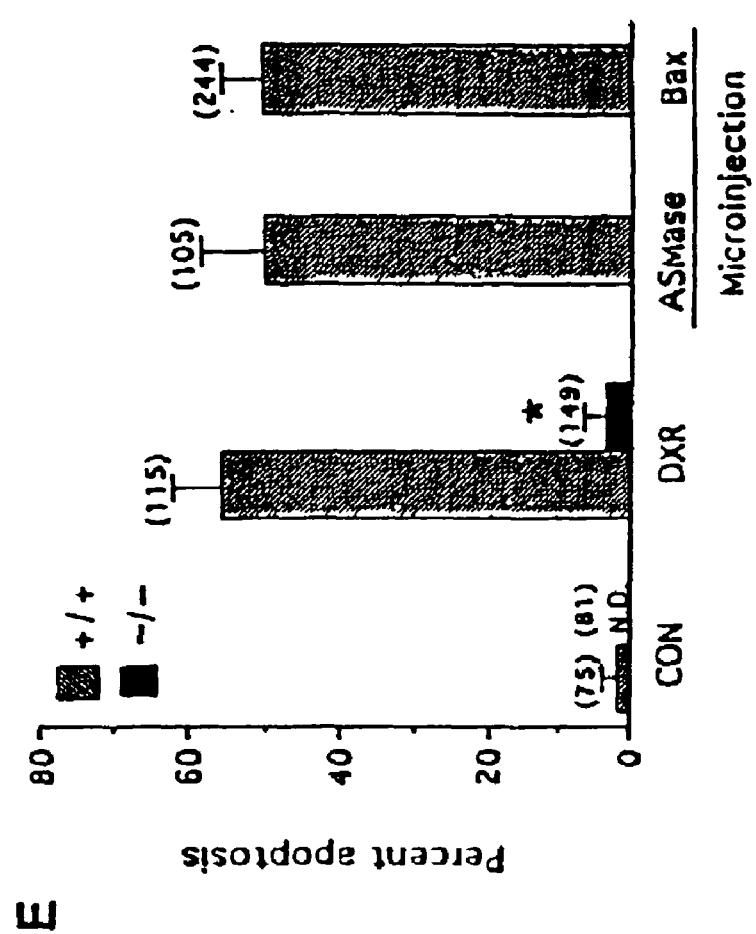

*Figure 3c*  *Figure 3e*

*Figure 3a*  *Figure 3b*

PROTECTION OF THE FEMALE REPRODUCTIVE SYSTEM FROM NATURAL AND ARTIFICIAL INSULTS

RELATED APPLICATION

The present application is a continuation-in-part of U.S. patent application Ser. No. 09/503,852, filed Feb. 15, 2000, now U.S. Pat. No. 7,195,775 and claims benefit thereof.

GOVERNMENT SUPPORT

The invention described herein was supported by grants from the U.S. Department of Energy, the National Cancer Institute, the National Institute on Aging, the National Institute of Child Health and Human Development, the National Institute of Environmental Health Sciences, the Steven and Michelle Kirsch Foundation and Vincent Memorial Research Funds. The government has certain rights in the invention.

FIELD OF THE INVENTION

The present invention relates to methods for protecting the female reproductive system against natural or artificial insults by administering a composition comprising an agent that antagonizes one or more acid sphingomyelinase (ASMase) gene products. In particular, this invention relates to a method of protecting ovaries from cancer therapy regimens, chemotherapy and radiotherapy, by administering to women a composition containing sphingosine-1-phosphate, or an analog thereof, prior to, concomitant with, and/or subsequent to the therapy. Methods to enhance ovarian functions, ameliorate symptoms of menopause, and improve the success of in vitro fertilization are also disclosed.

I. BACKGROUND OF THE INVENTION

Female gonads house a finite number of meiotically-arrested germ cells (oocytes) enclosed within primordial follicles that serve as the stockpile of eggs released at ovulation at each menstrual cycle for potential fertilization. Gougeon, *Endocr Rev.* 17, 121 (1996); Morita & Tilly, *Dev. Biol.* 213 (1999). Once depleted, the ovarian germ cell pool cannot be replenished. Thus, exposure of women to a wide spectrum of agents that damage the ovary, such as chemotherapeutic agents and radiotherapy, generally leads to premature menopause and irreversible sterility. Waxman, *Soc. Med.* 76, 144 (1983); Familiari et al., *Hum. Reprod.* 8, 2080 (1993); Ried & Jaffe, *Semin. Roentgenol.* 29, 6 (1994); and Reichman & Green, *Monogr. Natl. Cancer Inst.* 16, 125 (1994).

Apoptotic cell death plays a fundamental role in normal germ cell endowment and follicular dynamics in the ovary. Tilly & Ratts, *Contemp. Obstet. Gynecol.* 41, 59 (1996); Tilly, *Rev. Reprod.* 1, 162 (1996); and Tilly et al., *Cell Death Differ.* 4, 180(1997). Cell fate in the ovary is likely dependent on the actions of several proteins recently identified as key determinants of cell survival or death (Adams & Cory, *Science* 281, 1322 (1998); Green, *Cell* 94,695 (1998); Thornberry & Lazebnik, *Science* 281,1312 (1998); Reed, *Oncogene* 17,3225 (1998); Korsmeyer, *Cancer Res.* 59,1693 (1999). Among these identified in the ovary are p53 (Tilly et al., *Endocrinology* 136, 1394 (1995); Keren-Tal et al., *Exp. Cell Res.* 218, 283 (1995); and Makrigiannakis et al., *J. Clin. Endocrinol. Metab.* 85,449 (2000)), members of the bcl-2 gene family (Tilly et al., *Endocrinology* 136-232 (1995); Ratts et al., *Endocrinology* 136,3665 (1995); Knudson et al., *Science* 270,99 (1995); Perez et al., *Nature Med.* 3 1228 (1997); Kugu et al., *Cell Death Differ.* 5, 67 (1998); Perez et al., *Nature Genet.* 21, 200 (1999), and members of the caspase gene family (Flaws et al., *Endocrinology* 136, 5042 (1995); Perez et al., *Nature Med.* 3, 1228 (1997); Maravei et al., *Cell Death Differ.* 4, 707 (1997); Kugu et al., *Cell Death Differ.* 5, 67 (1998); Boone & Tsang, *Biol. Reprod.* 58, 1533 (1998); Bergeron et al., *Genes Dev.* 13, 1304 (1998); and Perez et al., *Mol. Hum Reprod.* 5, 414 (1999)).

In addition, ceramide, a recently identified lipid second messenger associated with cell death signaling (Spiegel et al., *Curr. Opin. Cell Biol.* 8, 159 (1996); Hannun, *Science* 274, 1855(1996); and Kolesnick & Kronke,*Annu. Rev. Physiol.* 60,643 (1998)) has been implicated in the induction of apoptosis in the ovary (Witty et al., *Endocrinology* 137, 5269 (1996); Kaipia et al., *Endocrinology* 137,4864(1996); and Martimbeau & Tilly, *Clin. Endocrinol.* 46, 241(1997)).

Since the initial discovery of the sphingomyelin pathway, numerous studies have been published on the potential role of ceramide in signaling cell death (Hannun, (1996) id.; and Kolesnick & Kronke (1998) id.). A central role for ceramide, a pro-apoptotic sphingolipid (Kolesnick & Krönke, *Annu. Rev. Physiol.*, 60:643 (1998)) derived from either sphingomyelin hydrolysis or de novo synthesis, in mediating death of oocytes exposed to anti-cancer therapies, has recently emerged (Perez et al., *Nat. Med.*, 3:1228 (1997); and Morita, Y. et al.,*Nat. Med.* 6, 1109-1114 (2000)). Oocyte apoptosis is suppressed by disruption of the acid sphingomyelinase gene or by sphingosine-1-phosphate therapy (Morita, Y. et al.,*Nat. Med.* 6, 1109-1114 (2000)). Whether or not cells die in response to ceramide elevations is, however, at least partly dependent upon the rate at which ceramide is metabolized. It is now known that ceramide can also be metabolized via ceramidase to sphingosine, which is then phosphorylated by sphingosine kinase to generate sphingosine-1-phosphate (S1P), a potent antagonist of ceramide-promoted apoptosis (Cuvillier et al., *Nature* 381, 800 (1996); Spiegel et al., *Ann. N.Y. Acad. Sci* 845, 11 (1998); and Spiegel, *J. Leukoc. Biol.* 65, 341 (1999)).

In some cell types, S1P can effectively counterbalance stress-kinase activation and apoptosis induced by membrane-permeant ceramide analogs or external stressors known to work through elevations in intracellular ceramide levels. Therefore, a rheostat model has been proposed in which cell fate is controlled by shifts in the balance between ceramide and S1P levels. However, the physiologic importance of ceramide, and that of sphingomyelin hydrolysis as a whole, in activating developmental or homoeostatic paradigms of apoptosis have recently been questioned by some investigators (Hofmann & Dixit, *Trends Biochem. Sci* 23, 374 (1998); and Watts et al., *Cell Death Differ.* 6, 105 (1999)). In particular, Hofmann et al., describe a lack of developmental defects that should be the consequence of impaired apoptosis in the acid sphingomyelinase (ASMase) gene knockout mouse as substantive evidence against a role for ASMase-catalyzed sphingomyelin hydrolysis and ceramide in signaling cell death (Kolesnick & Kronke (1998) id.)

Earlier studies using pharmacologic and genetic approaches have shown that several other components of the programmed cell death regulatory pathway in oocytes, including Bcl-2 family members (Ratts et al., *Endocrinology* 136, 3665 (1995); Perez et al., *Nat. Med.* 3, 1228 (1997); Morita et al., *Mol. Endocrinol.* 13, 841 (1999); Perez et al., *Nat. Genet.* 21,200(1999)); and caspases (Perez et al.,(1997) id.; Bergeron et al., *Genes Dev.* 12, 1304 (1998)), are required for oocyte survival or death. However, cell lineage specificity will certainly be an important issue to consider based on observations that p53, a classic signaling molecule for cancer therapy-induced tumor cell destruction (Ko & Prives, *Genes Dev.* 10, 1054 (1996); and Ding et al., *Crit. Rev. Oncog.* 9, 83 (1998)), is completely dispensable for oocyte death initiated by cancer therapy (Perez et al., (1997) id.)

Although the sensitivity of oocytes to cancer therapy, and the potential role of ceramide in signaling cell death are reported, as evidenced above, little is known regarding the mechanisms responsible for female germ cell destruction. Recently, it has been shown that female mouse oocytes undergo a type of cell death, referred to as apoptosis, when exposed in vitro to a prototypical anti-cancer drug (doxorubicin, 14-hydroxydaunorubicin, Adriamycin®). (Perez et al., (1997) id.) Moreover, it was shown that culture of mouse oocytes in vitro with sphingosine-1-phosphate protected the oocytes from death induced by subsequent doxorubicin exposure for up to 24 hours. However, the protection was only tested in vitro with only a single drug under a brief window of time, and thus in vivo application remained questionable. Also, the oocytes isolated for these in vitro tests are developmentally very different from the specific populations of oocytes that are destroyed by chemotherapy and radiotherapy in vivo. Due to the differences in oocytes, it is impossible to determine the relevance of data derived from these in vitro models to that which occurs in vivo. Thus, there remains a need for in vivo methods of protecting the female reproductive system from natural or artificial insult.

II. SUMMARY OF THE INVENTION

The present invention is the first to show that protection of the female reproductive system, in particular the oocytes, from natural or artificial insults that occur in vivo is achieved in vivo, and that this protection is accomplished by administration of a composition containing an agent that antagonizes activity or expression of one or more acid sphingomyelinase (ASMase) gene products. The invention demonstrates that such agents have promising therapeutic effects in combating ovarian failure, thus preserving fertility and normal ovarian functions under various adverse conditions.

Furthermore, the present invention also demonstrates that oocytes protected with S1P from an artificial insult in vivo remain competent to produce viable offspring which lack measurable anatomic, histologic, biochemical, or cytogenetic evidence of propagated genomic damage.

One embodiment of the invention provides a method of protecting the female reproductive system against a natural or an artificial insult comprising: administering a composition comprising an agent that antagonizes one or more acid sphingomyelinase (ASMase) gene products, in an amount sufficient to protect said female reproductive system from normal or pre-mature aging or destruction caused by said natural or artificial insult. The artificial insult comprises chemical insult, radiation insult, surgical insult, or a combination thereof. Natural insults to the reproductive system occur as a consequence of aging, genetic background, physiological factors, environmental factors, or other developmental and genetic factors. The artificial and natural insults treated by the methods of the present invention are those insults that occur in vivo, as opposed to, e.g., insults that occur to isolated tissues or cells.

According to an embodiment of the invention, the artificial insult comprises chemical insults, including for example, cytotoxic factors, chemotherapeutic drugs, hormone deprivation, growth factor deprivation, cytokine deprivation, cell receptor antibodies, and the like. Chemotherapeutic drugs include 5FU, vinblastine, actinomycin D, etoposide, cisplatin, methotrexate, doxorubicin, among others.

In accordance with another embodiment of the invention, the artificial insult comprises radiation insult, including ionization radiation, x-ray, infrared radiation, ultrasound radiation, heat, or a combination thereof. Radiation is administered to a patient through an invasive radiation therapy, a non-invasive radiation therapy, or both.

Protection of female's reproductive system is achieved in females in all age groups consisting of pre-reproductive age, reproductive age and post-reproductive age group.

One of the preferred agents of this invention is a small molecule compound comprising a lysophospholipid. More preferably the lysophospholipid is a sphingolipid compound, or an analog thereof. The most preferred agent of the invention is the compound of sphingosine-1-phosphate, or an analog thereof. The agent is administered ex vivo, in vivo, or in vitro. Preferred routes of administration include, orally, intravascularly, intraperitoneally, intra-uterine, intra-ovarian, subcutaneously, intramuscularly, rectally, topically, or a combination thereof. Intra-ovarian administration is achieved by methods, including, for example, by direct injection into the ovary. The injection is made to the ovary in vivo or ex vivo.

According to another embodiment of the invention, a method of preserving, enhancing, or reviving ovarian function in female mammals is disclosed. This method comprises administering to female mammals an effective amount of a composition comprising sphingosine-1-phosphate, or an analog thereof. The ovarian functions include fertility and normal menstrual cyclicity.

Yet another object of the invention is a method to prevent or ameliorate menopausal syndromes. Menopausal syndromes within the scope of this invention include somatic disorders, cognitive disorders, emotional disorders, and the like. The agent of the invention is administered on a regular daily, weekly, biweekly, monthly or annual intervals in order to achieve the intended therapeutic objective.

According to another object of the invention, an in vitro fertilization method is disclosed that comprises (a) obtaining at least one oocyte from a mammal; (b) incubating said oocyte in a medium containing a lysophospholipid, a sphingolipid, or sphingosine-1-phosphate, or an analog thereof, in an amount sufficient to maintain viability of said oocyte in culture; (c) fertilizing in vitro said oocyte with sperm to produce at least one fertilized oocyte (zygote); (d) culturing said fertilized oocyte to produce an embryo; and (e) transferring at least one embryo to the uterus of said mammal, wherein said at least one embryo develops to term in said mammal.

Yet still another embodiment of the invention provides a method of protecting a female reproductive system from damage caused by a treatment for a disease, disorder, or condition comprising administering to a mammalian female a treatment effective to treat a disease, disorder, or condition, wherein said treatment is selected from the group consisting of chemical treatment, radiological treatment, surgical treatment, and combinations thereof; and a composition comprising an agent that antagonizes one or more acid sphingomyelinase (ASMase) gene products, in an amount sufficient to protect said reproductive system from damage and/or destruction caused by said treatment, and wherein said reproductive system remains competent to produce viable offspring as measured by the lack of anatomic, histologic, biochemical, or cytogenetic evidence of propagated genomic damage to the offspring. The administration of the composition is terminated prior to exposure of the female reproductive system to the treatment, concomitant with the treatment and/or subsequent to the treatment.

III. BRIEF DESCRIPTION OF THE FIGURES

FIG. 1. Postnatal oocyte hyperplasia results from ASMase gene disruption. Number of non-atretic primordial, primary and small preantral follicles in young adult (day 42 postpartum) wild-type (hatched bars) and ASMase gene knockout (solid bars) female mice (mean±SEM, n=3 mice per genotype; $P<0.05$ versus respective wild-type value).

FIG. 2. ASMase-deficiency or sphingosine-1-phosphate treatment attenuates programmed cell death in the female germline during fetal gametogenesis. (A) Rate of programmed cell death in the germline of ovaries obtained from wild-type (+/+) or ASMase-mutant (−/−) female fetuses following in vitro culture without hormonal support. Each data point represents the mean (±SEM) number of non-apoptotic germ cells remaining per ovarian section, and the results are the combined data from 6 fetal ovaries per genotype ($P<0.05$ versus respective wild-type value). (B) Effects of fumonisin-B1 (FB1) and S1P on germ cell survival in wild-type fetal ovaries cultured for 72 hours without hormonal support (mean±SEM, n=6 fetal ovaries per group). Over one-half of the starting population of germ cells (0 h or Time 0) is preserved after 72 hours of hormone deprivation by either ASMase gene disruption or by S1P treatment.

Figure 3D:
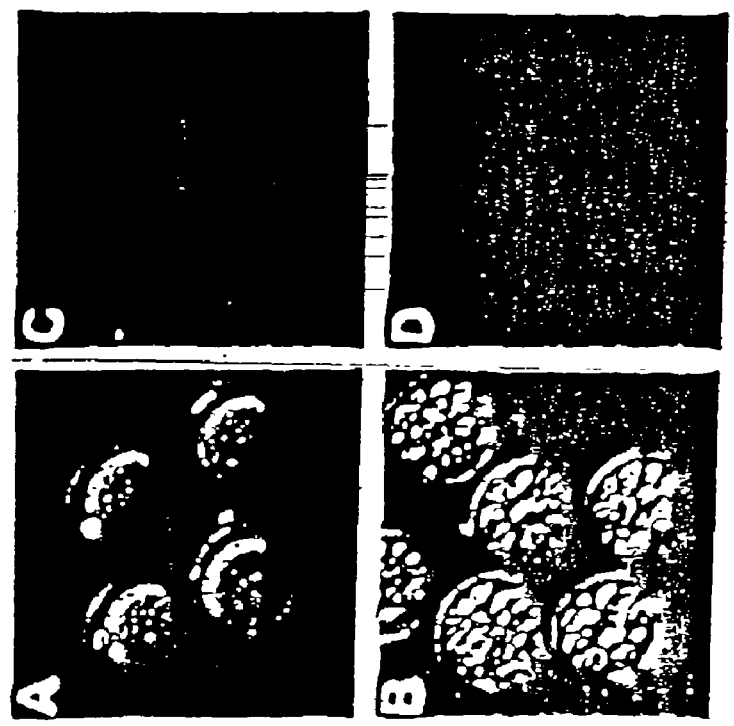

FIG. 3. Cell autonomous nature of the germline programmed cell death defect caused by ASMase gene disruption or S1P treatment. Representative analysis of cellular morphology (A, B) and of DNA integrity as assessed by the comet assay (C, D) in pools of non-apoptotic oocytes (ASMase-deficient oocytes treated with doxorubicin or DXR; A, C) and apoptotic oocytes (wild-type oocytes treated with DXR; B, D). (E) Apoptotic cell death response in wild-type (+/+) versus ASMase-deficient (−/−) oocytes cultured without (control, CON) or with 200 nM DXR for 24 hours, or in wild-type oocytes microinjected with human recombinant ASMase or human recombinant Bax. Mean±SEM from 3 or more independent experiments with the total number of oocytes used per group indicated over the respective bar, $P<0.05$ versus respective wild-type value, N.D., none detected. For both ASMase and Bax microinjection, a significant ($P<0.05$) increase in apoptosis was observed versus those levels observed in comparable numbers of vehicle-injected oocytes cultured in parallel (20±5%; mean±SEM, n=3 or more independent experiments).

Figure 4:
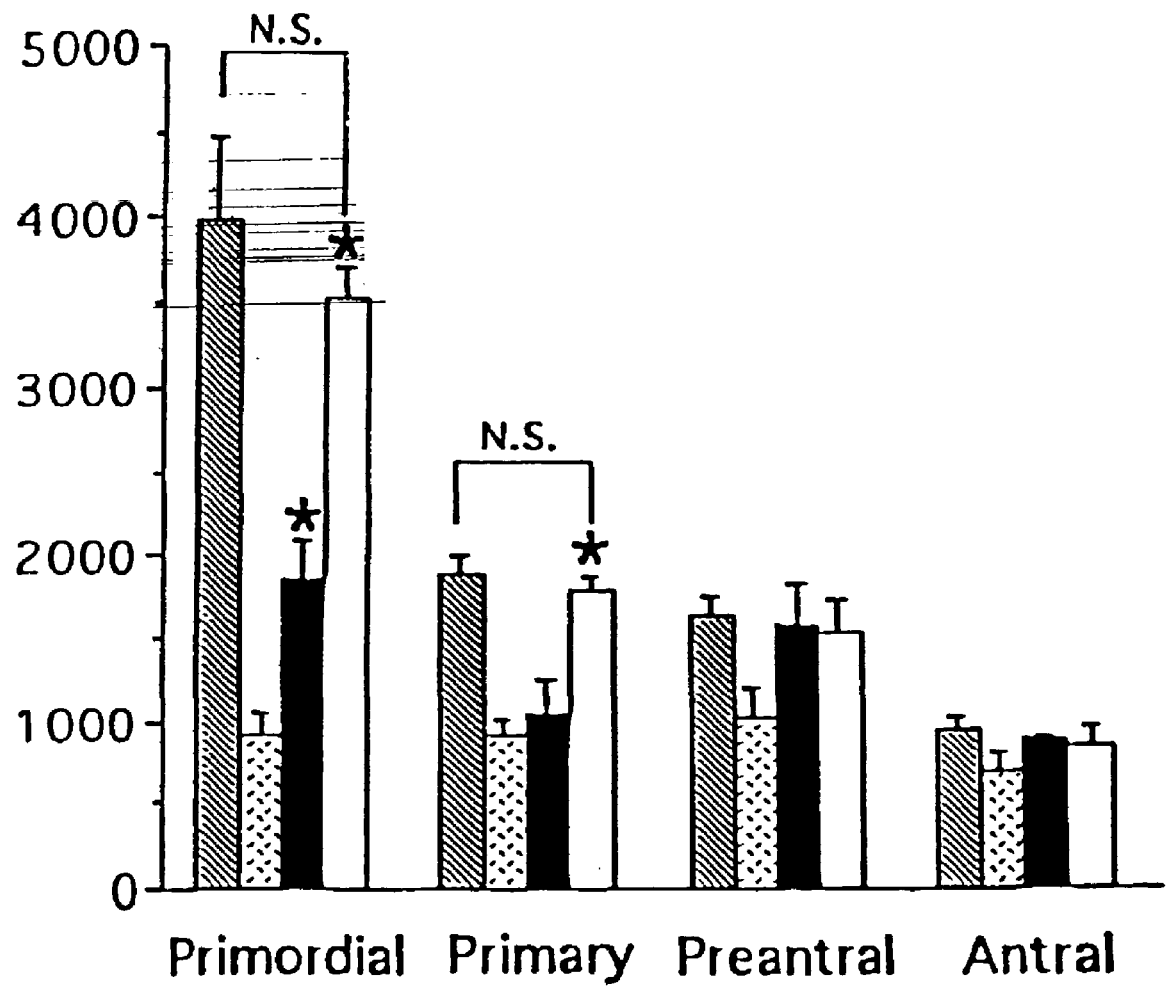

FIG. 4. Complete protection of the female germline from radiation-induced death in vivo by S1P administration. Morphometric analysis of the number of non-atretic oocyte-containing follicles at the four indicated stages of development remaining in vehicle (PET)-or S1P-treated ovaries 14 days after a single treatment with 0.1 Gy of ionizing radiation (mean±SEM, n=3 mice; $P<0.05$ versus 0 µM S1P receiving radiation treatment; N.S., not significantly different).

Figure 5:
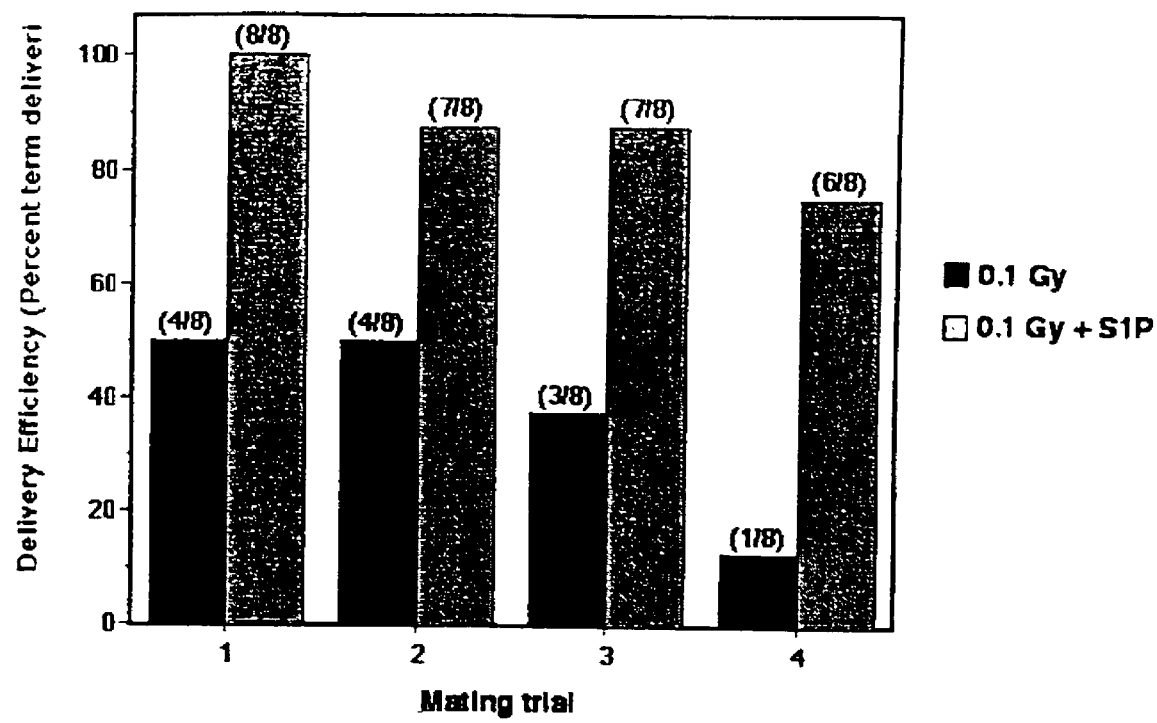

FIG. 5. S1P preserves fertility in irradiated female mice. Female mice, pre-treated with vehicle (n=8) or 200 µM of S1P (n=8) prior to irradiation (0.1 Gy), were mated 2 months later with adult wild type males, and then at successive 2 month intervals for a total of 4 matings per female. The ratios provided in parentheses over each bar depict the number of successful pregnancies out of the 8 mice per group mated per trial.

Figure 6:
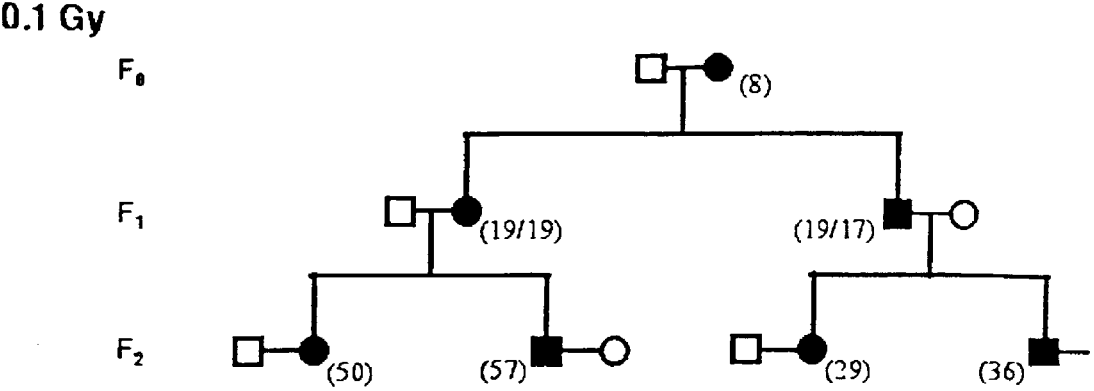
Figure 6:
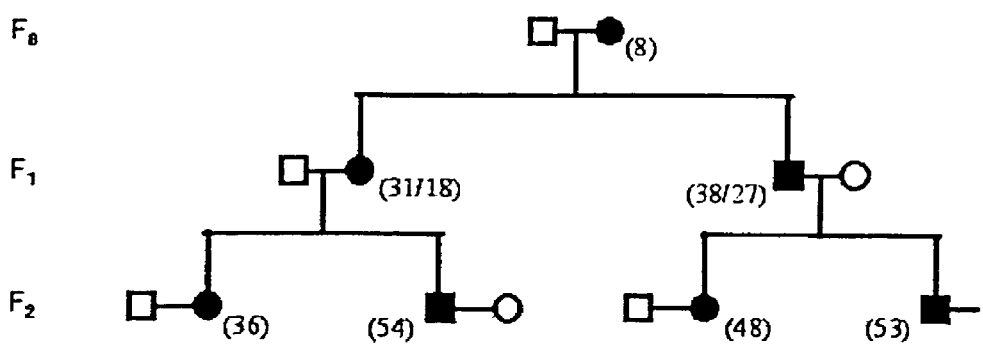

FIG. 6. Mating pedigree of vehicle-treated and S1P-treated irradiated female mice ($F_0$). Squares and circles represent males and females, respectively. Filled symbols represent treated mice or their progeny, whereas open symbols represent wild-type mice used for breeding purposes. Values in parentheses are the total number of mice studied in that group. In $F_1$ mice, the additional number in parentheses indicates the number of mice used for mating.

Figure 7:
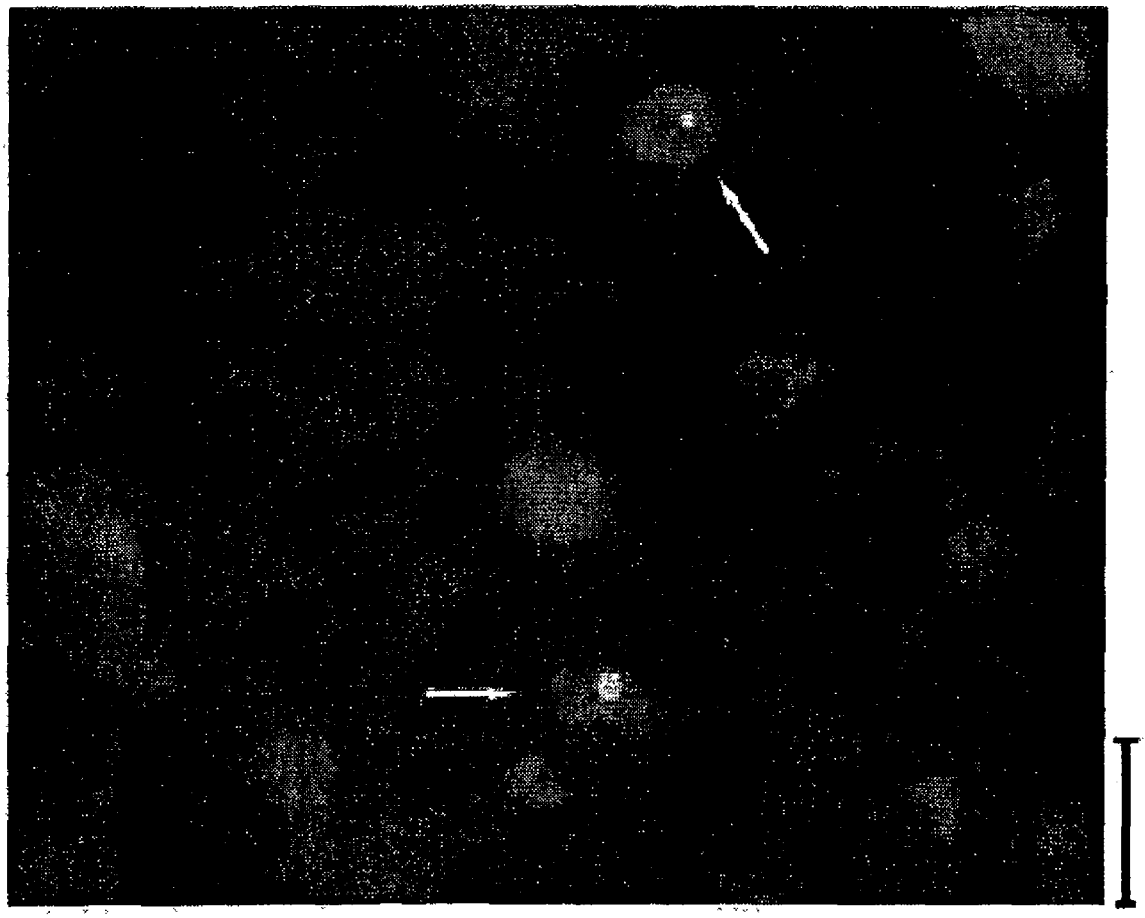
Figure 7:
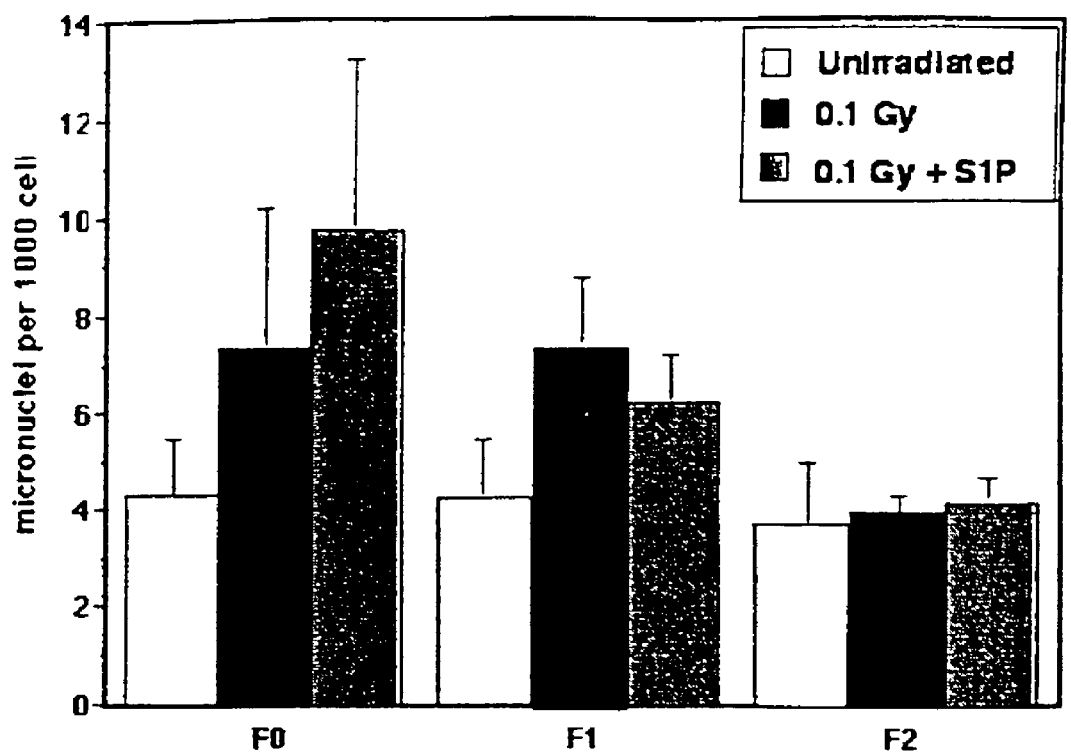

FIG. 7. Frequency of micronuclei in $F_0$, $F_1$, and $F_2$ mice. (A) Typical micronuclei (arrow). Scale Bar, 10 µm (B) Analysis of $F_0$, $F_1$, and $F_2$ animals, compared to non-irradiated age-matched controls (0 Gy). The data represent the mean ±95% confidence limit.

IV. DETAILED DESCRIPTION OF THE INVENTION

This invention, as described herein, relates that compositions containing a therapeutic agent that is an ASMase gene product inhibitor, administered in vivo, protect the female reproductive system from stress signals or insults induced by natural or artificial factors, including damage caused by treatment for a disease, condition, or disorder. The invention further relates that administration of these compositions protects the female reproductive system such that offspring of females exposed to natural or artificial insult remain viable as demonstrated by their lack of measurable anatomic, histologic, biochemical or cytogenetic evidence of propagated genomic damage.

Apoptosis is a mechanism by which cells are programmed to die under a wide range of physiological, biochemical and developmental stimuli. Apoptosis is also an important cellular response to a large variety of stress signals, induced by natural or artificial factors. Acid sphingomyelinase (ASMase) gene disruption is shown to suppress normal apoptotic deletion of oocytes, leading to ovarian hyperplasia. Ex vivo, ASMase −/− oocytes or wild-type oocytes treated with an agent, capable of antagonizing one or more ASMase gene products, resist developmental and anticancer treatment-induced apoptosis, thereby confirming cell autonomy of the death defect.

The invention, as disclosed and described herein, provides for a germ cell-autonomous death defect, leading to increased survival of oocytes, caused by ASMase-deficiency. Cell autonomous death is reversed by inhibition of ASMase gene products, which inhibition causes a significant hyperplasia of the female germline during fetal ovarian development. These data, demonstrate that antagonizers of ASMase gene products confer significant protection against natural or artificial insults on oocytes in vivo, or in vitro and, therefore, offer a new route for rapid therapeutic development to combat premature ovarian failure, and to prolong ovarian function and fertility in women.

The ASMase antagonizers, or the "agent" according to this invention, include any compound, that suppresses or inhibits activity and/or expression of one or more acid sphingomylinase (ASMase) gene products in vitro, ex vivo, or in vivo. The agent comprises, for example, any lipid, lysophospholipid, sphingolipid, protein, peptide, polypeptide, nucleic acid molecule, including DNA, RNA, DNA/RNA hybrids or an antisense molecule, small molecules, antibiotics, and the like. The terms protein, peptide, and polypeptide are used interchangeably herein.

A preferred agent according to the invention is a small molecule. In a more preferred embodiment of the invention, the agent comprises lysophospholipids, and most preferably, the agent is sphingosine-1-phosphate (S1P), a pharmaceutically acceptable salt thereof, or an analog thereof. Examples of analogs of sphingosine-1-phosphate, include but are not limited to, N,N-dimethylsphingosine-1-phosphate; N,N,N-trimethylsphingosine-1-phosphate; N-acetylsphingosine-1- phosphate; N-acylsphingosine-1-phosphate; sphingosine-1, 3-diphosphate; sphingosine-3-phosphate; sphingosine-1-thiophosphate; N,N-dimethylsphingosine-1-thiophosphate; N,N,N-trimethylsphingosine-1-thiophosphate; or pharmaceutically acceptable salts thereof.

Sphingosine-1-phosphate is shown to be safe and without side effects on the ovaries. In one general embodiment of the invention, as disclosed herein, in vivo administration of the agent of the invention prior to an artificial insult resulted in a significant preservation of the germ cell reserve with complete protection of the quiescent (primordial) and growing (primary, preantral) follicle populations in ovaries exposed to the insult.

According to one general embodiment of the invention, artificial insults are the consequence of a therapy against a disease or a disorder. The disease or disorder comprises, for example, cancer, rheumatoid arthritis, angioplasty, or restenosis. Cancer includes, for example, colon carcinoma, pancreatic cancer, breast cancer, ovarian cancer, fibrosarcoma, myxosarcoma, liposarcoma, chondrosarcoma, osteogenic sarcoma, chondroma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, acute lymphocytic leukemia and acute myelocytic leukemia, chronic leukemia and polycythemia vera, lymphoma (Hodgkin's disease and non-Hodgkin's disease), multiple myeloma, Waldenstrom's macroglobulinemia, or immunoglobulin heavy chain diseases.

Artificial insults, according to the invention described herein, include chemical, radiation, and surgical insults. Examples of chemical insults include, cytotoxic factors, chemotherapeutic drugs, hormone deprivation, growth factor deprivation, cytokine deprivation, cell receptor antibodies and the like. Further non-limiting examples include TNF-alpha, TNF-beta, IL-1, INF-gamma, IL-2, insulin-like growth factor, transforming growth factor beta1, vascular endothelial growth factor, fibroblast growth factor, 5FU, vinblastine, actinomycin D, etoposide, cisplatin, methotrexate, doxorubicin, and the like.

In accordance with another embodiment of the invention, the insult is a radiation insult. It is shown that the germlines of female mammals exposed to radiation are seriously damaged and administration of the composition of the invention in vivo or ex vivo protects oocytes from destruction induced by a therapeutically-relevant dose of ionizing radiation.

Radiation insult, according to the invention disclosed herein, encompasses both non-invasive (external) and invasive (internal) radiation therapies. In an external radiation therapy, treatment is affected by radiation sources outside the body, whereas in an invasive radiation therapy treatment is affected by radiation sources planted inside the body. The representative diseases treated by non-invasive or invasive radiation therapy include, for example, cancer, rheumatoid arthritis, angioplasty, or restenosis.

Invasive radiation therapy encompasses, for example, selective internal radiation therapy (SIRT), incorporation of the radioactive materials into small particles, microspheres, seeds, wires and the like. These objects are directly implanted into the various tissue, organs, or their respective arterial blood supply within the body.

Various methods for introducing radiation into an area treated for stenosis are known. Some methods deliver radiation in a solid medium, while others utilize liquid sources. For example, a procedure in reducing the restenosis rate is the introduction of radiation energy into the interior of the vessel. This procedure, known as "intravascular radiation therapy" (IRT) has been shown to inhibit fibroblast and smooth muscle cell hyperplasia.

U.S. Pat. No. 5,059,166, issued to Fischell, discloses an IRT method that relies on a radioactive stent that is permanently implanted in the blood vessel after completion of the lumen opening procedure. U.S. Pat. No. 5,302,168, issued to Hess, teaches use of a radioactive source contained in a flexible catheter. U.S. Pat. No. 5,503,613, issued to Weinberger, uses a liquid filled balloon to guide a solid source wire to a treatment site. U.S. Pat. No. 5,616,114, issued to Thornton et al., describes an apparatus and method for delivering liquid radiation into a balloon-tipped catheter. Radiation therapies disclosed by aforementioned patents, are disclosed merely as examples of radiotherapeutic regimens used to treat patients and are non-limiting.

The use of radioactive material in connection with therapies, such as those disclosed above, creates a risk of harmful exposure, both to the medical personnel and to patients. Precautionary measures need to be taken to protect against the harm caused by the leakage of liquid radiation into the blood stream during these therapies. Sensitive organs, such as the ovaries, are inevitably damaged depending on the invasiveness of the procedure used. The invention disclosed herein protects ovaries of both patients and medical personnel from a risk of harm caused by exposure to radiation during such therapies.

Radiation is emitted from a variety of radionuclides. These radionuclides encompass, for example, beta-ray emitters, gamma-ray emitters, or a radionuclide that emits both beta-ray and gamma-ray. Further examples of radionuclides include, Strontium 90, Iridium 192, Phosphorous 32, Rhenium 186, Rhenium 188, $^{198}$Au, $^{169}$Er, $^{166}$Ho, $^{153}$Sm, and $^{165}$Dy, which are chosen according to the purpose of treatment.

Other radiation sources include sources used in nuclear magnetic resonance diagnosis in which the central ion of the complex salt must be paramagnetic. In particular, the radiation sources use the divalent and trivalent ions of the elements of atomic numbers 21-29, 42, 44 and 58-70. Suitable ions are, for example, the chromium(III), manganese(II), iron(II), nickel(II), copper(II), praseodymium(III), neodymium(III), samarium(III), ytterbium(III), gadolinium(III), terbium(III), dysprosium(III), holmium(III), erbium(III), and iron(III).

According to another embodiment of the invention disclosed herein, radiation insult includes ultrasound radiation. Ultrasound radiation is administered to patients, either alone or in combination with other therapies, for example, hormonal therapy, chemotherapy, or surgery. The therapeutic regimen is applied either preoperatively, i.e., to the tumor in situ or postoperatively, in the region of the tumor after removal of the primary cancerous lesion. The ultrasound therapy comprises both the invasive and non-invasive ultrasound treatments. The dosage of ultrasonic energy applied is, for example, above 22.5 watt/sec, and has a frequency in the range of, for example, about 1 KHz to about 3 MHz.

According to another embodiment of this invention, radiation insult includes, x-ray, infrared, and heat. Heat is used to selectively induce apoptosis in intended cells or tissues. Preferably heat is used to treat inflammation. The term inflammation includes inflamed atherosclerotic plaques, restenosis, and arteritis such as that found in systemic lupus, myocarditis of the autoimmune etiology, arteriovenous fistulea, dialysis grafts or other vascular prosthesis. The phrase "treating inflammation" also includes treating a region of a vein prior to or after balloon angioplasty, or related interventions that could result in inflammation and subsequent thrombosis, acute closure or restenosis.

Heat may be transferred to the target cells by a variety of methods. For example, heat is transferred into an inflamed plaque in a blood vessel by means of a catheter, stent, or liquid heat. Catherter or stents are heated electrically or with microwave or radio frequency radiation or other means. Heat is also generated from internal or external devices, such as radiofrequency sources outside the body. The present invention protects ovaries from the risk of over-exposure to heat waves or liquid heat during heat therapy.

Natural insults, as defined herein, include damages resulting from physiological, biochemical or developmental processes occurring in a female body. A manifest natural insult is apoptosis due to aging. Natural insults are influenced, for example, by genetic background of the female, environmental effects, or both. The functional life span of female gonads is defined by the size and rate of depletion of the endowment of oocytes enclosed within follicles in the ovaries at birth. This continuous loss of oocytes throughout life, referred to by many as the female biological clock, is driven by a genetic program of cell death that is controlled by physiological and biochemical pathways and players and is conserved from worms to humans (Morita & Tilly (1999) id.) This invention, as disclosed herein, demonstrates the effect of antagonizers of ASMase gene products in combating normal or pre-mature germ cell depletion in a female mammal.

Without being limited to any specific mechanism of action underlying the invention described herein, one possible mechanism for the effect of antagonizers of ASMAse gene products is through preventing apoptosis of granulosa cells as well as, or instead of, directly preventing apoptosis of oocytes. Granulosa cells support, nourish, and help to mature oocytes throughout postnatal life.

Examples of disease and disorders resulting from a natural insult include, disturbances in menstruation, abnormal uterine bleeding, abnormal ovulatory cycles, amenorrhea, pelvic pain, sexual dysfunction, in fertility, menstrual cyclicity, and pre-mature menopause among others.

Other insults include surgical insults wherein a woman's reproductive system, in part or in whole, is surgically removed. In particular, hormonal imbalance, resulting from the removal of one ovary, is fully or partially restored by administration of the therapeutic agent of the invention.

Reproductive system includes any cell, tissue, organ, and tract that are involved in part or in whole in sexual reproduction. Cells include variety of somatic cells, for example, granulosa cells that nourish and mature oocytes, as well as germ cells.

Included within the scope of this invention are methods to protect women's ovaries from natural and artificial insults, not only to keep them fertile, but also to preserve enough ovarian function to prevent or delay menopause and its associated disorders. Women are subject to natural or artificial insult in any age group. These age groups are pre-reproductive, reproductive or post-reproductive age groups. Pre-mature menopausal syndromes are initiated by a wide variety of artificial or natural conditions. Menopausal disorders, include, for example, somatic disorders such as osteoporosis, cardiovascular disease, somatic sexual dysfunction, loss of libido; cognitive disorders, such as loss of memory; emotional disorders, such as depression, and the like.

The composition of the invention is administered on a continuous or semi-continuous, or temporary basis, depending on the type of insult and objectives of the therapy intended. For example, if protection of the reproductive system from long term natural insults is intended, administration of the composition of this invention on a continuous or semi-continuous basis is preferred. In a continuous administration, the composition is generally administered regularly, on a predetermined interval, for an indefinite period of time. Predetermined intervals comprise daily, weekly, biweekly, or monthly, or yearly intervals.

If protection from artificial insults is intended, both short term and long term administration are suggested, depending on the type of insult and the objective of the therapy intended. An example of a short term administration is the administration to protect ovaries from radiation or chemical insults. In short term administration, the composition is administered, at least once, in a period of from about thirty days prior to immediately prior to exposure to the insult. More preferably the composition is administered from about fifteen days to about two days, and most preferably from about seven days to about two hours prior to exposure to the insult. The administration of the composition is terminated prior to ovarian exposure to the insult, or it is continued during exposure or after the exposure is terminated.

The dosage of the therapeutic agent is adjusted according to, for example, the duration and the objective of the treatment intended. A lower dosage of the agent is required in a more prolonged and continuous administration.

The administration is achieved in vitro, in vivo or ex vivo. The in vivo administration encompasses orally, intravascularly, intraperitoneally, intra-uterine, intra-ovarian, subcutaneously, intramuscularly, rectally, topically, or a combination thereof. Intra-ovarian administration is achieved by several methods, including, for example, by direct injection into the ovary. The injection is made to the ovary in vivo or ex vivo.

According to another aspect of this invention, an in vitro fertilization method is described that uses the therapeutic agent of this invention to protect the viability of the female germline at different stages of in vitro fertilization. These stages, include in vivo, ex vivo, and in vitro periods of fertilization and pregnancy. In vivo stages of fertilization and pregnancy include, for example, one or more of the following periods: the period prior to isolation of oocytes, the period after implantation of the embryo in the uterus, and the period during pregnancy. In vitro, and ex vivo stages include, for example, one or more of the following: cryopreservation of oocytes, culture or growth of oocytes prior to fertilization, fertilization stage, culture or growth of embryo post-fertilization.

Oocytes isolated from women are at different stages of development and are either mature or immature. Immature oocytes reach maturity under in vitro or in vivo conditions. In vitro fertilization, according to the invention, is achieved by the use of a mammal's own oocytes or a different mammal's oocytes. After the embryo is implanted in the subject mammal, in vivo administration of the therapeutic agent is terminated, or it is continued for a time period thereafter to ensure continued viability and normal development of the embryo in vivo.

The in vitro fertilization method according to the invention disclosed and described herein increases the chances of successful fertilization, pregnancy and normal development of the embryo in the uterus. Furthermore, it ensures availability of immature or mature oocytes for fertilization, and makes it possible to preserve fertility and increases availability of donor oocytes for women who do not have their own functional oocytes.

Also embraced within the scope of this invention are compositions comprising one or more agents of the invention in association with one or more non-toxic, pharmaceutically acceptable carriers and/or diluents and/or adjuvants (collectively referred to herein as "carrier" materials) and, if desired, other active ingredients.

According to an embodiment of the invention, the agent is combined with one or more adjuvants appropriate to the indicated route of administration. If administered per os, the compounds maybe admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Formulations for parenteral administration are, for example, in the form of aqueous or non-aqueous isotonic sterile injection solutions or suspensions. These solutions and suspensions are prepared, for example, from sterile powders or granules having one or more of the carriers or diluents mentioned for use in the formulations for oral administration. The compounds may be dissolved in water, polyethylene glycol, propylene glycol, ethanol, corn oil, cotton seed oil, peanut oil, sesame oil, benzyl alcohol, sodium chloride, and/or various buffers. Other adjuvants and modes of administration are well and widely known in the pharmaceutical art.

The compositions of the invention are adapted to be administered by any suitable route, and in a dose effective for the treatment intended. Therapeutically effective doses of the composition required to prevent or preserve the female reproductive system from insults are readily ascertained by one of ordinary skill in the art.

For oral administration, the composition is in the form of, for example, a tablet, capsule, suspension or liquid. The composition is preferably made in the form of a dosage unit containing a particular amount of the active ingredient. Examples of such dosage units are tablets or capsules. Preferably, the oral units contain an amount of active ingredient from about 1 to 1000 mg, more preferably from about 25 to 500 mg, and most preferably from about 100 to 250 mg. A suitable daily dose may vary widely, however, a dose of from about 0.01 to 3000 mg/kg body weight, or from about 0.1 mg to about 100 mg/kg of body weight per day is preferred. A more preferred dosage will be a range from about 1 mg to about 100 mg/kg of body weight. Most preferred dosage is a dosage in a range from about 1 to about 50 mg/kg of body weight per day.

The dosage regimen of the agents and/or compositions of this invention is selected in accordance with a variety of factors and thus may vary widely. A main factor to consider is the objective of therapy, for example, protecting female germline from radiation or chemotherapy, prolonging fertility, preventing menopause, preserving normal menstrual cyclicity, ameliorating or preventing post-menopausal conditions, are among many therapeutic objectives that are intended and encompassed within the scope of the invention. Other factors include, for example, the age, weight, severity and type of the insult, the route of administration, and the type of therapeutic agent employed.

In a particular embodiment, the present invention comprises a method of preserving fertility in a female mammal comprising administering to said female mammal:

(a) a treatment selected from the group consisting of chemical treatment, radiological treatment, surgical treatment, and combinations thereof; and (b) an ASMase gene antagonizer such as a lysophospholipid in an amount sufficient to preserve fertility.

By "preserving fertility" or "to preserve fertility" upon administration of a lysophospholipid is meant that administration of a lysophospholipid to a female mammal that is also administered a treatment results in increased fertility (e.g., greater number of pregnancies, greater number of offspring) as compared to a similar female mammal that is not administered the lysophospholipid but is administered the treatment. By "similar female mammal" is meant an individual of the same species and of approximately the same age and general condition of health.

By "administering to said female mammal" a lysophospholipid is meant that the lysophospholipid is administered (a) to the intact, living mammal, as by, e.g., intravenous delivery, oral delivery, or direct injection to the ovaries; or (b) ex vivo, e.g., to oocytes that have been taken from a mammal and are then returned to the body of the mammal. Accordingly, in the method described above, a lysophospholipid is not administered to oocytes that have been isolated from the female mammal where the oocytes are not thereafter returned to the body of the mammal.

"Chemical treatment" includes chemical insults, including for example, cytotoxic factors, chemotherapeutic drugs, hormone deprivation, growth factor deprivation, cytokine deprivation, cell receptor antibodies, and the like. Chemotherapeutic drugs include 5FU, vinblastine, actinomycin D, etoposide, cisplatin, methotrexate, doxorubicin, among others.

"Radiological treatment" includes radiation insults, including the use of ionizing radiation, treatment with radionuclides, treatment from radiation sources outside or inside the body, treatment with radiation sources used in nuclear magnetic resonance diagnosis, as well as treatment with ultrasound, x-rays, infrared radiation, and heat.

"Surgical treatment" includes surgical insults, as defined herein.

In particular embodiments, the lysophospholipid is a sphingolipid or sphingosine-1-phosphate. In other embodiments, the lysophospholipid is an analog of sphingosine-1-phosphate.

In particular embodiments, the "amount sufficient to preserve fertility" is an amount selected from the group consisting of: a dose of from about 0.01 to 3000 mg/kg of body weight, a dose of from about 0.1 to 1500 mg/kg of body weight, a dose of from about 1 to 1000 mg/kg of body weight, a dose of from about 3 to 500 mg/kg of body weight, and a dose of from about 10 to 100 mg/kg of body weight.

The invention will be more fully understood by reference to the following examples. These examples are not to be construed in any way as limiting the scope of this invention. All literature cited herein is specifically incorporated by reference.

V. EXAMPLES

Example 1

Histomorphometric Evaluation of Oocyte Endowment

Ovaries are fixed (0.34 N glacial acetic acid, 10% formalin, 28% ethanol), embedded in paraffin, and serially sectioned (8 µM). The serial sections from each ovary are aligned in order on glass microscope slides, stained with hematoxylin/picric methyl blue, and analyzed for the number of healthy (non-atretic) oocyte-containing primordial, primary and small preantral follicles as described by Perez et al. *Nat. Genet.* (1999) id. incorporated by reference herein in its entirety.

Example 2

Histomorphometric Evaluation of Wild Type and ASMase −/− Ovaries

ASMase −/− mice are generated as described by Horinouchi et al., *Nat. Genet.* 10, 288 (1995), incorporated herein by reference in its entirety. The histomorphometric evaluation of the oocyte endowment of wild type mice and ASMase −/− sisters shows that sphingomyelin hydrolysis is a key event in generating death signals in the developing female germline. Compared with their wild-type sisters, ASMase −/− females possess over $1.1 \times 10^3$ more quiescent oocyte-containing primordial follicles per ovary, as well as significant hyperplasia of the growing (primary and small preantral) follicle populations. Results are presented in Table 1 and FIG. 1.

TABLE 1

Postnatal Oocyte Hyperplasia Results From ASMase Gene Disruption

| Follicles | +/+ | −/− | P value |
| --- | --- | --- | --- |
| Primordial | 19120 ± 602 | 30480 ± 2397 | P < 0.01 |
| Primary | 707 ± 93 | 1573 ± 141 | P < 0.01 |
| Preantral | 13 ± 13 | 160 ± 46 | P < 0.05 |

Number of non-atretic oocyte-containing primordial follicles endowed in the ovarian reserve, and numbers of growing (primary and small preantral) follicles, in wild-type (+/+) and ASMase-mutant (−/−) female mice at day 4 postpartum (mean±SEM, n=3 mice per genotype).

The ovarian oocyte reserve remains significantly elevated in ASMase −/− female mice in young adult life (FIG. 1), well prior to the onset of any organ abnormalities or Niemann-Pick disease-like symptoms that occurs in ASMase −/− mice during postnatal life.

To determine the basis of the extensive oocyte hyperplasia in ASMase −/− neonates, fetal ovaries are harvested from wild-type and mutant mice at embryonic day 13.5 (e13.5) for in vitro culture as a model to recapitulate the events surrounding germline death that occurs as a normal component of female gametogenesis. A time-dependent activation of programmed cell death is observed in the germline of wild-type fetal ovaries cultured without hormonal support for up to 72 hours (FIG. 2A). By comparison, the rate of germ cell apoptosis is significantly attenuated in ASMase-deficient fetal ovaries cultured in parallel (FIG. 2A). These findings indicate that there exists an ovarian-intrinsic cell death defect in the ASMase-deficient mouse, and point to enhanced survival of the developing germline during oogenesis as the mechanism underlying the enlarged oocyte pool seen in mutant females at birth.

Example 3

Treatment with Ceramide Synthase Inhibitor

In order to show that sphingomyelin hydrolysis, as opposed to ceramide synthesis, is important for generating ceramide as a death signal, wild-type fetal ovaries are maintained in vitro for 72 hours and various concentrations (5-500 µM) of a ceramide synthase inhibitor, fumonisin-B1 (FB1) are applied to these ovaries. The results show that this treatment does not alter survival rates in the female germline (FIG. 2B). Importantly, however, and in support of the rheostat model, the reduced incidence of germ cell apoptosis conveyed by ASMase-deficiency is recapitulated by culturing wild-type fetal ovaries with increasing concentrations of S1P (FIG. 2B). Equivalent levels of in vitro germ cell survival are obtained by either ASMase gene knockout (FIG. 2A) or by S1P treatment (FIG. 2B).

Example 4

Cell Autonomous Nature of Response

To demonstrate that germline survival is a cell autonomous or a germline-intrinsic response, individual oocytes are isolated from adult wild-type and ASMase −/− female mice, and are cultured ex vivo with or without the anti-cancer drug, doxorubicin (DXR), to induce apoptosis. In addition to assessments of cellular morphology and caspase activation, some oocytes in each group are processed for DNA cleavage analysis as an endpoint for cell death using the Trevigen Comet Assay kit. The apoptotic event is elicited in wild-type, but not ASMase-deficient, oocytes by DXR (FIG. 3E).

Example 5

Microinjection Experiment

Human recombinant acid sphingomyelinase is synthesized and purified as described by He et al., *Biochim. Biophys.* Acta 1432, 251 (1999), incorporated herein by reference in its entirety. Six picoliters of vehicle or of a 1 mg/ml stock of the enzyme are microinjected into single oocytes using a Zeiss Axiovert 135 inverted microscope equipped with Narishige micromanipulators and a PLI-100 pico-injector. Oocytes that survive the microinjection procedure (>75%) are then cultured and assessed for the occurrence of apoptosis. Furthermore, microinjection of human recombinant Bax protein into single oocytes and assessments of apoptosis are made as described by Perez, et al. (1997) id. Microinjection of human recombinant Bax protein into oocytes duplicates the pro-apoptotic effects of both human recombinant ASMase microinjection and anti-cancer drug treatment (FIG. 3E). For both ASMase and Bax microinjection, a significant (P<0.05) increase in apoptosis is observed versus those levels observed in comparable numbers of vehicle-injected oocytes cultured in parallel (20±5%; mean±SEM, n=3 or more independent experiments).

Example 6

In Vitro Oocyte Cultures

Female mice (43 days of age post-partum; Charles River Laboratories, Wilmington, Mass.) are superovulated with 10 IU of equine chorionic gonadotropin (eCG orPMSG) followed by 10 IU of human chorionic gonadotropin (hCG) 48 h later. Mature oocytes are collected from the oviducts 16 h after hCG injection. Cumulus enclosed oocytes are denuded by a 1-min incubation in 80 IU/ml of hyaluronidase, followed by three washes with culture medium. The medium used for all culture experiments is human tubal fluid (Irvine Scientific, Santa Ana, Calif.) supplemented with 0.5% bovine serum albumin (BSA).

Oocytes are cultured in 0.1 ml drops of culture medium (8-10 oocytes/drop) under paraffin oil and incubated with or without DXR (200 nM) and/or fumonisin-B1, sphingosine-1-phosphate or benzyloxycarbonyl-Val-Ala-Asp-fluoromethylketone (zVAD-FMK) for 24 h at 37° C. in a humidified atmosphere of 5% $CO_2$-95% air. At the end of the incubation period, oocytes are fixed, stained with Hoechst 33342 and checked microscopically for morphological changes characteristic of apoptosis (condensation, budding, cellular fragmentation, and chromatin segregation into apoptotic bodies). The percentage of oocytes that go through apoptosis out of the total number of oocytes cultured per drop in each experiment is then determined, and all experiments are independently repeated four to ten times with different mice.

Example 7

In Vitro Embryo Cultures

Female mice are superovulated with eCG followed by hCG treatment (see above) and placed with fertile males immediately after hCG injection. Sixteen hours after mating, one-cell embryos (confirmed by the presence of two polar bodies) are harvested from the ampullae and denuded of cumulus cells by a 1-min hyaluronidase treatment. Embryos are then maintained in vitro in IITF supplemented with 0.5% BSA in absence or presence of 200 nM DXR. Under in vitro conditions, one-cell embryos progressed to the morula stage of development within 72 h (see in vitro oocyte cultures above for details of methodology and culture conditions). See, Perez et al.(1997) id., incorporated by reference herein in its entirety.

Example 8

Bax-Null Mice

In vitro experiments: mature oocytes are harvested from wild-type and Bax-null adult female mice at approximately 6 weeks of age using the gonadotropin superovulation regimen described above. Following hyaluronidase removal of cumulus cells, oocytes are incubated for 24 h without or with 200 nM DXR, after which the occurrence of apoptosis is assessed and described under in vitro oocyte cultures.

In vivo experiments: age-matched adult wild-type and Bax-null female mice are given two intraperitoneal injections of DXR (10 mg/kg of body weight) 1 week apart, starting at approximately 8 weeks of age post partum. One week following the second injection, ovaries are collected, fixed, embedded in paraffin, serial-sectioned, and stained with hematoxylin/picric methyl blue. Follicular morphology and numbers of immature (primordial) follicles present in each ovary are then assessed as detailed previously.

Example 9 p53-Null Mice

Mature oocytes are collected from adult wild-type and p53 null female mice by superovulation, and incubated with or without 200 nM DXR for 24 h. Following culture, the occurrence of apoptosis is assessed as described above (see, Example 6: in vitro oocyte cultures).

Example 10

S1P Protection Against Radiation

Young adult (postpartum day 40) wild-type female mice are anesthetized, and dorsal incisions are made to retrieve and expose the ovaries. Five µl of vehicle (PET) are injected into the bursa of one ovary of the pair while 5 µl of a stock of either 0.5 or 2 mM S1P, prepared in PET, are injected into the bursa of the contralateral ovary. Based on an estimated bursal cavity volume of 50 µl, the final concentrations of S1P in the bursal cavity for ovarian exposure following administration of the 0.5 and 2 mM stocks are approximately 50 and 200 µM, respectively. The ovaries are returned to the peritoneal cavity, the incisions are sutured, and the mice are allowed to recover for a 2 hour pretreatment period prior to a single exposure to 0.1 Gy of abdominally-directed ionizing radiation. After two weeks, ovaries are collected, coded, and processed for histomorphometric evaluation of non-atretic oocyte-containing follicle numbers as described above (see Example 1). In the absence of irradiation, the number of follicles at any stage of development in S1P-treated ovaries does not significantly differ from the number of corresponding follicles in vehicle-treated ovaries.

Nearly complete destruction ($LD_{80}$) of the oocyte-containing primordial follicle pool is observed in vehicle-treated ovaries of mice two weeks after a single exposure to 0.1 Gy of ionizing radiation (FIG. 4). In contrast, in vivo administration of S1P two hours prior to irradiation results in a significant and dose-dependent preservation of the germ cell reserve, with complete protection of the quiescent (primordial) and growing (primary, preantral) follicle populations in ovaries exposed to the highest dose of S1P prior to irradiation (FIG. 4).

Moreover, since oocyte viability, growth and function are required for continued development of follicles from a quiescent to mature state (see, Morita & Tilly (1999) id., incorporated herein by reference in its entirety), the observation that ovaries pretreated with the highest dose of S1P prior to irradiation retain a completely normal distribution of oocyte-containing follicles at all stages of development (i.e., identical to the non-irradiated controls) at two weeks post-irradiation (FIG. 4) suggests that the protected oocytes are indeed viable and functional.

Example 11

Irradiation and Treatment of Mice

Eight-week old C57BL/6J female mice (Jackson Laboratories) are anesthetized by intraperitoneal injection of Avertin (30 μl of a 1.25% stock solution per gram of body weight; Aldrich Chemical Co.), and dorsal incisions are made to retrieve and expose the ovaries. Five μl of vehicle (5% polyethylene glycol, 2.5% ethanol, and 0.8% Tween-80, or PET) or of a stock of 2 mM S1P (BIOMOL) prepared in PET are injected into the bursa surrounding each ovary (see Example 10). Based on an estimated bursal cavity volume of 50 μl, the final concentration of S1P following this procedure is 200 μM. The ovaries are returned to the peritoneal cavity, the incisions are sutured, and the mice are allowed to recover for a 2-h pre-treatment period. Mice are then given a single dose of 0.05 or 0.1 Gy of abdominally directed ionizing radiation, using a cesium$^{137}$ source (Shepherd Mar-I, Model 68) at a dose rate of 0.7 Gy min$^{-1}$.

Example 12

Mating Trials

To evaluate whether the acute protection of oocytes by S1P also results in long-term preservation of ovarian function and fertility, mating trials are initiated 2 months after irradiation. For these studies, 8-week old C57BL/6J female mice are given intrabursal injections of vehicle or a maximally effective dose of S1P (0.2 mM final concentration in the bursal cavity) two hours before exposure to 0.1 Gy of ionizing radiation, delivered as a single dose. Previous studies showed that this dose of radiation results in loss of approximately 80% of the primordial oocyte reserve within 2 weeks in vehicle-treated mice, whereas ovaries of S1P-treated animals given ionizing radiation are indistinguishable from non-irradiated controls (see Example 10). Females, irradiated without or with S1P pre-treatment, are then mated with non-irradiated C57BL/6J males beginning 2 months post-irradiation. The $F_0$ females are caged with adult (2-4 month old) wild type C57BL/6J males for 15 d. As a control to assure the fertility of the males, each is mated to a female of proven fertility. After delivery, pups of first time mothers are fostered while pups of subsequent litters are maintained with their natural mothers. There is no increase in the frequency of rejection of pups by irradiated mothers whether or not those mothers are treated with S1P. The $F_0$ female mice are bred again with a new wild type male two weeks after the pups are weaned, and the process is repeated for a total of 4 matings.

As shown in FIG. 5, only 50% of vehicle-treated irradiated females deliver litters during the first mating trial, which drops to 12.5% by the fourth trial. In contrast, all of the S1P-treated irradiated females initially deliver litters, and even after one year 75% of these mice remain fertile (P<0.001 vs. vehicle-treated irradiated females). Historical data show a 92% fertility rate in the C57BL/6J strain within the first year of life, with an average litter size of 6.2±0.2 pups per litter (Nagasawa, H., Miyamoto, M. & Fujimoto M. Reproducitivity in inbred strains of mice and project for their efficient production. *Experimental Animals* 22, 119-26 (1973). In the present study, litter sizes in the vehicle-treated irradiated group average 5.6±0.6 pups per mating (p=0.32 vs. untreated C57BL/6J females), whereas litter sizes average 6.1±0.4 pups per mating in the S1P-treated irradiated group. No phenotypic or behavioral abnormalities are noted in $F_1$ offspring for up to 18 months of age.

It is next examined whether preservation of ovarian function and fertility might result in propagation of genomic damage to the $F_2$ progeny. To generate $F_2$ offspring, $F_1$ males and females are each bred at 2 months of age with adult (2-4 month old) wild type C57BL/6J females or males, respectively (see FIG. 6 for details). Again, no gross phenotypic or behavioral abnormalities are detected in this second generation of offspring.

When the $F_1$ animals reach 18-20 months of age and the $F_2$ animals reach 12-16 months of age, all mice are euthanized and subjected to gross necropsy and biochemical analysis. Organs from a subgroup of 65 randomly selected animals in the two different generations are also subjected to complete histologic analysis. No gross histologic or biochemical abnormalities are found (Table 2).

Necropsies

Eighteen to 20 month-old $F_1$ mice, and 12-16 month-old $F_2$ mice, are euthanized and gross pathology is assessed immediately upon death. In a total of 484 mice, the heart, lung, stomach, small and large intestine, liver, salivary gland, kidney, urinary bladder, brain, cervical spinal cord, muscle, bone, bone marrow, skin, pituitary, thyroid, pancreas, adrenal, lymph node, spleen, thymus, testis (males), seminal vesicle (males), prostate (males), ovary (females), and uterus (females) are evaluated. Any organ showing gross abnormalities is fixed with 10% paraformaldehyde, encased in paraffin, and stained with hematoxylin and eosin for in-depth histologic analysis. Furthermore, histology on all organs is performed on 65 randomly selected mice of different generations ($F_1$ or $F_2$), different genders, and different experimental treatments. From an additional 28 randomly-selected mice, blood is collected by cardiac puncture for hematologic analysis, and in 9 animals full differential counts are performed. Differential white cell counts are also performed in all mice displaying a pathological phenotype.

TABLE 2

Lack of pathologic abnormalities in SiP protected offspring

| | | Pathology | | Hematology | | | | | | |
|---|---|---|---|---|---|---|---|---|---|---|
| | N | Gross necropsy | Histology | WBC (4.0-15.0) | RBC (9.1-9.9) | HGB (13.6-16.2) | HCT (42.2-48.1) | MCV (45.6-48.5) | MCH (15.0-16.3) | MCHC (28.3-38.4) |
| 0 Gy | 5 | NSL | NSL | 8.7 ± 3.2 | 9.2 ± 0.2 | 14.4 ± 0.4 | 45.7 ± 1.3 | 49.7 ± 1.3 | 15.7 ± 0.4 | 31.5 ± 0.6 |
| 0.1 Gy | 37 | NSL | NSL | 11.2 ± 0.3 | 9.7 ± 0.4 | 14.6 ± 0.2 | 46.9 ± 0.8 | 49.0 ± 0.3 | 15.3 ± 0.2 | 31.2 ± 0.5 |
| 0.1 Gy + S1P | 69 | Enlarged uterus Perineal tumor | LI in liver (2) LI in lung (3) Mucometra Lipoma | 10.9 ± 0.9 | 9.3 ± 0.2 | 14.2 ± 0.2 | 45.4 ± 0.9 | 49.1 ± 0.4 | 15.3 ± 0.2 | 31.4 ± 0.3 |

TABLE 2-continued

Lack of pathologic abnormalities in SiP protected offspring

|  |  | Pathology |  | Hematology |  |  |  |  |  |  |
|---|---|---|---|---|---|---|---|---|---|---|
|  | N | Gross necropsy | Histology | WBC (4.0-15.0) | RBC (9.1-9.9) | HGB (13.6-16.2) | HCT (42.2-48.1) | MCV (45.6-48.5) | MCH (15.0-16.3) | MCHC (28.3-38.4) |
| 0 Gy | 10 | NSL | NSL | 8.1 ± 1.7 | 9.4 ± 0.4 | 14.5 ± 0.3 | 46.9 ± 1.7 | 49.8 ± 1.2 | 15.7 ± 0.4 | 31.5 ± 0.6 |
| 0.1 Gy | 174 | Dermatitis Mesenteric tumor | LI in lung (3) Liver Kidney (2) Lymphoma | 10.7 ± 0.5 | 9.4 ± 0.1 | 14.4 ± 0.1 | 46.7 ± 0.5 | 49.9 ± 0.2 | 15.6 ± 0.1 | 31 ± 0.2 |
| 0.1 Gy + S1P | 189 | Dermatitis (3) Cyst in right ovary Alopecia Traumatic injury | LI in lung (7) Liver (3) Kidney Ovarian cyst | 11.0 ± 0.6 | 9.4 ± 0.2 | 14.9 ± 1.0 | 46.3 ± 1.1 | 49.2 ± 0.4 | 15.9 ± 1.1 | 30.8 ± 0.8 |

N, number of animals evaluated per condition; NSL, no significant lesions; LI, lymphocytic infiltration; Numbers in parenthesis indicate animals per group. WBC, Total White Blood Cell Count ($\times 10^9$/l); RBC, Red Blood Cell Count ($\times 10^{12}$/l); HGB, Hemoglobin (g/dl); MCV, Mean Corpuscular Volume (fl); MCH, Mean Corpuscular Hemoglobin (pg); MCHC, Mean Corpuscular Hemoglobin Content (g/dl); PLT, platelets ($\times 10^9$/l). Data represent mean ±95% confidence limit. The WBC, RBC, HGB, HCT, MCV, MCH, and MCHC data are from Foster, HL, Small, JD and Fox, JG, The Mouse in Biomedical Research Vol. III, Academic Press, NY 1983, pp: 294-308; and the PLT data are from Sanderson, JH and Phillips, CE. An Atlas of Laboratory Animal Dermatology. Clarendon Press, Oxford, UK 1981, pp. 88-125.

Example 13

Evaluation of DNA Damage in $F_0$ Oocytes

To test for DNA damage in the germ line of the $F_0$ population, female mice are examined 8 weeks after treatment with 0.05 or 0.1 Gy of ionizing radiation for evidence of DNA abnormalities in the germ line. Oocytes beginning to complete the first meiotic division are examined. Air-dried chromosome preparations are made using a modification of the technique described in Tarkowski, A. K. An air drying method for chromosome preparations from mouse eggs. *Cytogenics* 5, 394-400 (1966). Briefly, oocytes at the germinal vesicle stage are liberated from mature antral follicles of ovaries from treated and control $F_0$ females at 8-10 weeks post-irradiation. Oocytes are cultured for 2 h in Waymouth's medium (Life Technologies) supplemented with 10% fetal bovine serum and 0.23 mM sodium pyruvate, as described previously (Woods, L. M. et al Chromosomal influence on meiotic spindle assembly: abnormal meiosis I in female Mlh1 mutant mice. *J. Cell Biol.* 145, 1395-1406 (1999)). At the end of the culture period, oocytes exhibiting nuclear envelope breakdown, indicative of resumption of the first meiotic division, are fixed to obtain chromosomes at diakinesis-metaphase I. At this stage, chromosomes condense in preparation for division but homologues remain physically connected by chiasmata. Oocytes are placed in a 1% citrate solution, transferred individually to a small drop of acidified water on a microscope slide, and fixed in situ with several drops of methanol:acetic acid (3:1, v:v). For analysis, slides are stained with 50 ng ml$^{-1}$ of 4',6-diamidino-2-phenylindole (DAPI; Sigma Chemical Co.), and scored by two independent observers, who are unaware of the treatment status of the individual females. Only cells with 20 pairs of homologous chromosomes are included in the analysis, and DNA damage is scored as cells exhibiting one or more breaks in a chromosome arm or an illegitimate recombination event between non-homologous chromosomes (cross-talk; Hassold, T. & Hunt, P. To err (meiotically) is human: the genesis of human aneuploidy. *Nat. Rev. Genet.* 2, 280-291 (2001)).

Table 3 shows that irradiation induces a significant dose-dependent reduction in the average number of oocytes recovered from mature antral follicles of vehicle-treated animals ($p < 0.01$ vs. 0 Gy). This is accompanied by a dose-dependent increase in DNA damage in those oocytes induced to complete the first meiotic division by in vitro culture ($p < 0.01$ vs. 0 Gy). When compared with vehicle-treated irradiated (0.1 Gy) mice, more oocytes are recovered from mature follicles in the ovaries of S1P-treated irradiated females ($p < 0.01$ vs. 0.1 Gy). However, there is no increase in the percentage of the oocyte population manifesting DNA damage in S1P-treated irradiated females when compared to vehicle-treated irradiated mice, despite the fact that S1P essentially protects the entire oocyte population from apoptotic death following radiotherapy (Morita, Y. et al Oocyte apoptosis is suppressed by disruption of the acid sphingomyelinase gene or by sphingosine-1-phosphate therapy. *Nat. Med.* 6, 1109-1114 (2000)).

TABLE 3

DNA Damage in $F_0$ Oocytes Scored at Diakinesis/Metaphase I

|  | n | Average Oocytes/o (mean ± SEM) | Total Scorable Oocytes | Oocytes with Breaks/ Crosstalk (% of total) |
|---|---|---|---|---|
| 0 Gy | 3 | 28.0 ± 4.5 | 35 | 1 (2.9%) |
| 0.05 Gy | 8 | 25.4 ± 2.9 | 94 | 13 (13.8%) |
| 0.05 Gy + S1P | 8 | 30.8 ± 3.9 | 110 | 18 (16.4%) |
| 0.1 Gy | 11 | 15.1 ± 1.4[1] | 72 | 16 (22.2%) |
| 0.1 Gy + S1P | 8 | 23.1 ± 2.5[2] | 86 | 24 (27.6%) |

[1]($p < 0.01$ vs. 0 Gy)
[2]($p < 0.01$ vs. 0.1 Gy)

Similar results are obtained with females examined 10 weeks after irradiation. These data, which suggest that S1P-treated female mice retain a much larger reserve of undamaged oocytes for procreation, are in keeping with the fact that the vehicle-treated irradiated females become progressively infertile in successive mating trials to a much greater extent than the S1P-treated females (FIG. 5).

Example 14

Micronuclei Assay

To evaluate the possibility of transgenerational transmission of DNA damage, the frequency of micronuclei is used as a sensitive indicator of the extent of propagated genomic damage (Trott, K. R., Jamali, M., Manti, L. & Teibe, A. Manifestations and mechanisms of radiation-induced genomic instability in V-79 Chinese hamster cells. *Int. J. Radiat. Biol.* 74, 787-791 (1998); Manti, L., Jamali, M., Prise, K. M., Michael B. D. & Trott, K. R. Genomic instability in Chinese hamster ovary cells after exposure to X rays or alpha particles of different mean energy transfer. *Radiat. Res.* 147, 22-28 (1997)). Tail blood samples from 16-18 month old non-irradiated, vehicle-treated and irradiated, or S1P-treated and irradiated $F_0$ mice, 16-18 month old $F_1$ mice, or 12-16 month old $F_2$ mice, are smeared onto glass microscope slides coated with acridine orange (Shinko Corporation, New York, N.Y.), and coded prior to analysis. The frequency of micronuclei is then assessed in the $10^3$ polychromatic erythrocytes by flourescence microscopy (Hayashi, M., Morita, T., Kodama, Y., Sofuni, T., & Ishidate, M., Jr. The micronucleus assay with mouse peripheral blood reticulocytes using acridine orange-coated slides. *Mutat. Res.* 245, 245-249 (1990)), after which the slides are decoded for data interpretation.

FIG. 7A shows cells with typical positive micronuclei. The frequency of micronuclei in non-irradiated, vehicle-treated irradiated or S1P-treated irradiated $F_0$ animals is presented in FIG. 7B. A small increase in the frequency of micronuclei over non-irradiated controls is observed in vehicle- and S1P-treated $F_0$ animals receiving 0.1 Gy of radiation, which is statistically significant in the S1P-treated group (P<0.01). This increase is not due to a few animals showing unusually elevated micronuclei frequency, but rather to a small increase in all irradiated animals. However, there is no significant difference in the frequency of micronuclei in vehicle-treated versus S1P-treated irradiated mice. Even more important, the frequency of micronuclei in the $F_1$ and $F_2$ progeny of the S1P-treated irradiated mothers is similar to that observed in the respective progeny of the vehicle-treated irradiated mothers as well as in age-matched non-irradiated controls (FIG. 7B).

These studies demonstrate that S1P-treated protection of the female germ line from radiotherapy does not propagate discernible genomic damage at the anatomic, histologic, biochemical, or cytogenetic level.

REFERENCES

1. Hannun, *Science*, 274:1855 (1996).
2. Cuvillier et al., *Nature*, 381:800 (1996).
3. Hofinann & Dixit, *Trends Biochem. Sci.*, 23:374 (1998).
4. Watts et al., *Cell Death Differ.*, 6:105 (1999).
5. Horinouchi et al., *Nat. Genet.*, 10:288 (1995).
6. Perez et al., *Nat. Med.*, 3:1228 (1997).
7. Bergeron et al., *Genes Dev.*, 12:1304 (1998).
8. Moritaetal., *Mol. Endocrinol.*, 13:841 (1999).
9. Reynolds, J. *Nat. Cancer Inst.*, 91:664 (1999).
10. Morita & Tilly, *Dev. Biol.*, 213:1-17 (1999).
11. Perez et al., *Nat. Genet.*, 21:200 (1999).
12. Morita et al., *Endocrinology*, 140:941 (1999).
13. Bose et al., *Cell*, 82:405 (1995).
14. Merrill et al., *Toxicol. Appl. Pharmacol.*, 142:208 (1997).
15. Perez et al., *Mol. Hum. Reprod..*, 5:414 (1999).
16. Van Brocklyn et al., *J. Cell Biol.*, 142:229 (1998).
17. Van Brocklyn et al., *J. Biol. Chem.*, 274: 4626 (1999).
18. Edsall et al., *J. Neurosci.*, 17:6952 (1997).
19. Goetzl & An, *FASEB J.*, 12:1589 (1998).
20. Hla et al., *Biochem. Pharmacol.*, 58:201 (1999).
21. Gosden, *Nature*, 383:485 (1996).
22. Dong et al., *Nature*, 383:531 (1996).
23. Tilly & Robles in: *Molecular Biology in Reproductive Medicine*, Fauser et al., (Parthenon, New York, 1999), Chapter 5, pp. 79-101.
24. Briggs et al., in: *Molecular Biology in Reproductive Medicine*, Fauser et al., (Parthenon, New York, 1999) Chapter 12, pp. 251-269.
25. Ko & Prives, *Genes Dev.*, 10:1054 (1996).
26. Ding & Fisher, *Crit. Rev. Oncog.*, 9:83 (1998).
27. Cuvillier, *J. Biol. Chem.*, 273:2910 (1998).
28. Pastorino et al., *J. Biol. Chem.*, 274:31734 (1999).
29. He et al., *Biochim. Biophys. Acta.*, 1432:251 (1999).
30. Jüirgensmeier et al., *Proc. Natl. Acad Sci. USA*, 95:4997 (1998).
31. Tilly & Johnson in: *Apoptosis and Cancer Chemotherapy*, Hickman & Dive, (Humana Press, Totowa, N.J.), Chapter 17, pp. 257-273.
32. Kolesnick & Krönke, *Annu. Rev. Physiol.*, 60:643 (1998).
33. S. Spiegel, *J. Leukoc. Biol.*, 65:341 (1999).
34. S. Spiegel et al., *Ann. N.Y. Acad. Sci.*, 845:11 (1998).
35. Adams & Cory, *Science* 281, 1322 (1998).
36. Green, *Cell* 94, 695 (1998).
37. Thomberry & Lazebnik, *Science* 281, 1312 (1998).
38. Reed, *Oncogene* 17, 3225 (1998).
39. Korsmeyer, *Cancer Res.* 59, 1693 (1999).
40. Tilly et al., *Endocrinology* 136, 1394 (1995).
41. Keren-Tal et al., *Exp. Cell Res.* 218, 283 (1995).
42. Makrigiannakis et al., *J. Clin. Endocrinol. Metab.* 85, 449 (2000)).
43. Tilly et al., *Endocrinology* 136-232 (1995).
44. Ratts et al., *Endocrinology* 136, 3665 (1995).
45. Knudson et al., *Science* 270, 99 (1995).
46. Kugu et al., *Cell Death Differ.* 5, 67 (1998).
47. Flaws et al., *Endocrinology* 136, 5042 (1995).
48. Maravei et al., *Cell Death Differ.* 4, 707 (1997).
49. Boone & Tsang, *Biol. Reprod.* 58, 1533 (1998).
50. Martimbeau & Tilly, *Clin. Endocrinol.* 46, 241(1997)).
51. Tilly, J. L., Commuting the death sentence: how oocytes strive to survive. *Nat. Rev. Mol. Cell Biol.* 2, 838-848 (2001)
52. Meirow, D. & Nugent, D. The effects of radiotherapy and chemotherapy on female reproduction. *Hum. Repro. Update* 7, 535-543 (2001).
53. Morita, Y. et al. Oocyte apoptosis is suppressed by disruption of the *acid sphingomyelinase* gene or by sphingosine-1-phosphate therapy. *Nat. Med.* 6, 1109-1114 (2000).
54. Nagasawa, H., Miyamoto, M. & Fujimoto M. Reproducitivity in inbred strains of mice and project for their efficient production. *Experimental Animals* 22, 119-26 (1973).
55. Trott, K. R., Jamali, M., Manti, L. & Teibe, A. Manifestations and mechanisms of radiation-induced genomic instability in V-79 Chinese hamster cells. *Int. J. Radiat. Biol.* 74, 787-791 (1998).
56. Manti, L., Jamali, M., Prise, K. M., Michael B. D. & Trott, K. R. Genomic instability in Chinese hamster ovary cells after exposure to X rays or alpha particles of different mean energy transfer. *Radiat. Res.* 147, 22-28 (1997).

57. Hayashi, M., Morita, T., Kodama, Y., Sofuni, T., & Ishidate, M., Jr. The micronucleus assay with mouse peripheral blood reticulocytes using acridine orange-coated slides. *Mutat. Res.* 245, 245-249 (1990).
58. Sankaranarayanan, K. & Chakraborty, R. Cancer predisposition, radiosensitivity, and the risk of radiation-induced cancers. 1. Background. *Radiat. Res.* 143, 121-143 (1995).
59. Dubrova, Y. E. et al. Human minisatellite mutation rate after the Chernobyl accident. *Nature* 380, 683-686 (1996).
60. Dubrova, Y. E. et al. Stage specificity, dose response, and doubling dose for mouse minisatellite germ-line mutation induced by acute radiation. *Proc. Natl. Acad. Sci. USA* 95, 6251-6255 (1998).
61. Niwa, O. & Kominami, R. Untargeted mutation of the maternally derived mouse hypervariable minisatellite allele in $F_1$ mice born to irradiated spermatozoa. *Proc. Natl. Acad. Sci. USA* 98, 1705-1710 (2001).
62. Satoh, C. & Kodaira, M. Effects of radiation on children. *Nature* 383, 226 (1996).
63. Kodaira, M., Satoh, C., Hiyama, K. & Toyama, K. Lack of effects of atomic bomb radiation on genetic instability of tandem-repetitive elements in human germ cells. *Am. J. Hum. Genet.* 57, 1275-1283 (1995).
64. Neel, J. V. Reappraisal of studies concerning the genetic effects of the radiation of humans, mice, and Drosophila. *Environ. Mol. Mutagen.* 31, 4-10 (1998).
65. Haimovitz-Friedman, A. et al. Ionizing radiation acts on cellular membranes to generate ceramide and initiate apoptosis. *J. Exp. Med.* 180, 525-535 (1994).
66. Tarkowski, A. K. An air drying method for chromosome preparations from mouse eggs. *Cytogenics* 5, 394-400 (1966).
67. Woods, L. M. et al. Chromosomal influence on meiotic spindle assembly: abnormal meiosis I in female Mlhl mutant mice. *J. Cell Biol.* 145, 1395-1406 (1999).
68. Hassold, T. & Hunt, P. To err (meiotically) is human: the genesis of human aneuploidy. *Nat. Rev. Genet.* 2, 280-291 (2001).
69. Bannerman, R. M. in *The Mouse in Biomedical Reserach Vol. III* (eds., Foster, H. L., Small, J. D., and Fox, J. G.) pp. 293-303 (Academic Press, New York, 1983).
70. Sanderson, J. H. & Phillips, C. E.) pp. 88-125 (Clarendon Press, Oxford, U.K., 1981).

What is claimed is:

1. A method of protecting the reproductive system of a female subject against a chemical or radiation insult, comprising: administering in vivo or ex vivo to said female subject a protective composition comprising an agent that antagonizes one or more acid sphingomyelinase (ASMase) gene products, wherein said agent is a lysophospholipid, in an amount sufficient to protect the reproductive system of said female subject from pre-mature aging or destruction caused by said chemical or radiation insult.

2. The method of claim 1, wherein said chemical insult comprises cytotoxic factors, chemotherapeutic drugs, hormone deprivation, growth factor deprivation, cytokine deprivation, cell receptor antibodies, or a combination thereof.

3. The method of claim 2, wherein said chemotherapeutic drug comprises; 5FU, vinblastine, actinomycin D, etoposide, cisplatin, methotrexate, doxorubicin, or a combination thereof.

4. The method of claim 1, wherein said radiation insult comprises ionization radiation, x-ray, infrared radiation, ultrasound radiation, heat, or a combination thereof.

5. The method of claim 1, wherein said radiation insult comprises an invasive radiation therapy, a non-invasive radiation therapy, or both.

6. The method of claim 1, wherein said female reproductive system comprises ovaries.

7. The method of claim 1, wherein said female reproductive system comprises oocytes.

8. The method of claim 1, wherein said female is in a reproductive age.

9. The method of claim 1, wherein said female is in a pre-reproductive age.

10. The method of claim 1, wherein said female is in a post-reproductive age.

11. The method of claim 1, wherein said lysophospholipid is a sphingolipid compound, or an analog thereof.

12. The method of claim 11, wherein said sphingolipid compound is sphingosine-1-phosphate, or an analog thereof.

13. The method of claim 1, wherein said protective composition is administered at least once from about fifteen days to about two days prior to exposure to said insult.

14. The method of claim 13, wherein said protective composition is administered at about seven days to about two hours prior to exposure to said insult.

15. The method of claim 1, wherein said protective composition is administered regularly for a continuous period of time.

16. The method of claim 1, wherein said protective composition is administered orally, intravascularly, intraperitoneally, subcutaneously, intramuscularly, inter-uterine, intra-ovarian, rectally, topically, or a combination thereof.

17. The method of claim 1, wherein said chemical or radiation insult is a result of a therapy against a disease or a disorder.

18. The method of claim 17, wherein said disease or disorder comprises cancer, rheumatoid arthritis, angioplasy, or restenosis.

19. The method of claim 18, wherein said cancer comprises colon carcinoma, pancreatic cancer, breast cancer, ovarian cancer, fibrosarcoma, myxosarcoma, liposarcoma, chondrosarcoma, osteogenic sarcoma, chondroma, angiosarcoma, endotheliosarcoma, lymphangiosarcoma, lymphangioendotheliosarcoma, synovioma, mesothelioma, Ewing's tumor, Iciomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, acute lymphocytic leukemia and acute myelocytic leukemia, chronic leukemia and polycythemia vera, lymphoma (Hodgkin's disease and non-Hodgkin's disease), multiple myeloma, Waldenstrom's macroglobulinemia, or a combination thereof.

20. The method of claim 1, wherein said administration is an ex vivo administration.

21. The method of claim 1, wherein said administration is an in vivo administration.

22. The method of claim 1, wherein said female subject is exposed to a chemical insult prior to said radiation insult.

23. The method of claim 1, wherein said female subject is exposed to a radiation insult prior to said chemical insult.

24. The method of claim 22, wherein administration of said protective composition is terminated prior to, concurrently with or subsequent to said chemical insult.

25. The method of claim 22, wherein administration of said protective composition is terminated prior to, concurrently with or subsequent to said radiation insult.

26. The method of claim 23, wherein administration of said protective composition is terminated prior to, concurrently with or subsequent to said chemical insult.

27. The method of claim 23, wherein administration of said protective composition is terminated prior to, concurrently with or subsequent to said radiation insult.

* * * * *